US008870839B2

(12) United States Patent
Roe et al.

(10) Patent No.: US 8,870,839 B2
(45) Date of Patent: Oct. 28, 2014

(54) DISPOSABLE ARTICLE INCLUDING A NANOSTRUCTURE FORMING MATERIAL

(75) Inventors: Donald Carroll Roe, West Chester, OH (US); David S. Salloum, West Chester, OH (US); Brandon Ellis Wise, Cincinnati, OH (US); Vladimir Gartstein, Mason, OH (US); Faiz Fiesal Sherman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 528 days.

(21) Appl. No.: 12/369,128

(22) Filed: Feb. 11, 2009

(65) Prior Publication Data
US 2009/0264836 A1  Oct. 22, 2009

Related U.S. Application Data

(60) Provisional application No. 61/046,891, filed on Apr. 22, 2008.

(51) Int. Cl.
| | | |
|---|---|---|
| A61F 13/15 | (2006.01) | |
| A61F 13/20 | (2006.01) | |
| A61F 13/84 | (2006.01) | |
| A61F 13/511 | (2006.01) | |
| A61K 8/02 | (2006.01) | |
| A61L 15/42 | (2006.01) | |
| D06M 23/08 | (2006.01) | |
| A61Q 17/00 | (2006.01) | |
| A61F 13/513 | (2006.01) | |

(52) U.S. Cl.
CPC ....... *A61F 13/51305* (2013.01); *A61F 13/8405* (2013.01); *A61F 13/511* (2013.01); *A61L 2400/12* (2013.01); *A61K 8/0208* (2013.01); *A61L 15/425* (2013.01); *D06M 23/08* (2013.01); *A61Q 17/00* (2013.01); *D06M 2200/05* (2013.01); *A61K 2800/412* (2013.01)
USPC ...................................... 604/385.01; 604/367

(58) Field of Classification Search
USPC .............................................. 604/367, 385.01
See application file for complete search history.

(56) References Cited

U.S. PATENT DOCUMENTS

| | | |
|---|---|---|
| 3,860,003 A | 1/1975 | Buell |
| 5,151,092 A | 9/1992 | Buell et al. |
| 5,221,274 A | 6/1993 | Buell et al. |

(Continued)

FOREIGN PATENT DOCUMENTS

| | | |
|---|---|---|
| EP | 1144536 B1 | 3/2004 |
| EP | 1144537 B1 | 3/2004 |

(Continued)

OTHER PUBLICATIONS

Biologie in Unserer Zeit, vol. 28, Issue No. 5 pp. 314-322, Barthlott, et al.

*Primary Examiner* — Michele M Kidwell
(74) *Attorney, Agent, or Firm* — Kathleen Y. Carter; John G. Powell

(57) ABSTRACT

A disposable treatment article or disposable cleaning article that includes a hydrophobic nanoporous material. The disposable treatment or cleaning article is configured to contact and apply the nanoporous material to a surface. The nanoporous material is configured to form hydrophobic nanostructures on a surface upon the application of an activation stimulus. The nanostructures provide an anti-contamination benefit to the surface upon which the nanostructures are disposed.

11 Claims, 11 Drawing Sheets

(56) References Cited

U.S. PATENT DOCUMENTS

| | | | |
|---|---|---|---|
| 5,500,216 A | 3/1996 | Julian et al. | |
| 5,554,145 A | 9/1996 | Roe et al. | |
| 5,569,234 A | 10/1996 | Buell et al. | |
| 5,580,411 A | 12/1996 | Nease et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,716,692 A | 2/1998 | Warner et al. | |
| 5,893,965 A | 4/1999 | Trokhan et al. | |
| 6,004,306 A | 12/1999 | Robles et al. | |
| 6,086,924 A * | 7/2000 | Sheridan | 424/724 |
| 6,217,890 B1 | 4/2001 | Paul et al. | |
| 6,660,363 B1 | 12/2003 | Barthlott | |
| 6,683,126 B2 | 1/2004 | Keller et al. | |
| 6,706,028 B2 | 3/2004 | Roe et al. | |
| 6,787,585 B2 | 9/2004 | Rose et al. | |
| 6,808,791 B2 | 10/2004 | Curro et al. | |
| 6,986,932 B2 | 1/2006 | Zink et al. | |
| 7,831,014 B2 * | 11/2010 | Green | 378/37 |
| 7,862,624 B2 * | 1/2011 | Tran | 8/115.6 |
| 2002/0150724 A1 | 10/2002 | Nun et al. | |
| 2003/0096083 A1 | 5/2003 | Morgan et al. | |
| 2003/0124301 A1 | 7/2003 | Oles et al. | |
| 2004/0014865 A1 | 1/2004 | Keller et al. | |
| 2004/0023824 A1 | 2/2004 | Zuechner et al. | |
| 2004/0154106 A1 | 8/2004 | Oles et al. | |
| 2004/0242097 A1 | 12/2004 | Hasenoehrl et al. | |
| 2004/0265533 A1 | 12/2004 | Hoying et al. | |
| 2005/0214541 A1 | 9/2005 | Berrada et al. | |
| 2005/0227563 A1 | 10/2005 | Bond | |
| 2006/0019114 A1 * | 1/2006 | Thies et al. | 428/522 |
| 2007/0128255 A1 | 6/2007 | Belcher et al. | |
| 2007/0190327 A1 * | 8/2007 | Gartstein et al. | 428/405 |
| 2010/0113857 A1 * | 5/2010 | Ramakrishna et al. | 588/299 |

FOREIGN PATENT DOCUMENTS

| | | |
|---|---|---|
| EP | 1144733 B1 | 6/2004 |
| GB | 2033751 | 5/1980 |
| JP | 07-197017 A | 8/1985 |
| WO | WO 03092646 | 11/2003 |

* cited by examiner 236  235  260
    230

DISPOSABLE ARTICLE INCLUDING A NANOSTRUCTURE FORMING MATERIAL

CROSS REFERENCE TO RELATED APPLICATIONS

This application claims the benefit of U.S. Provisional Application No. 61/046,891, filed Apr. 22, 2008.

FIELD OF INVENTION

The present disclosure relates to disposable treatment articles comprising a hydrophobic nanostructure forming material. Specifically, the present disclosure relates to disposable treatment articles that are adapted to transfer a hydrophobic nanostructure forming material to a bodily surface to form nanostructures thereon in order to reduce the potential for contaminants to cling or adhere to the bodily surface.

BACKGROUND OF THE INVENTION

Disposable treatment articles are known in the art and include, for example, disposable absorbent articles, disposable cleaning articles, and disposable delivery articles. Disposable absorbent articles are often used for receiving and storing bodily exudates. Examples of such disposable absorbent articles include diapers, diaper inserts, training pants, adult incontinence articles, and feminine hygiene articles such as sanitary napkins and bandages. Exemplary known disposable cleaning articles include paper towels, disposable non-woven wipes, toilet tissue, facial tissues, hair cleaning wipes, tooth cleaning wipes, and other implements that are adapted to remove contamination or other undesirable materials from a variety of surfaces (e.g., one or more bodily surfaces). Exemplary known disposable delivery articles include facial wipes, moistening wipes, protective hand wipes, cleansing pads, tooth whitening articles, and heat wraps. Disposable delivery articles are typically adapted to deliver one or more beneficial substances or energy such as, for example, a skin care active, lotion or heat, to a variety of surfaces such as one or more bodily surfaces.

Disposable absorbent articles may include a liquid permeable topsheet, a liquid impermeable backsheet and an absorbent core disposed between the topsheet and the backsheet. The absorbent core may be configured to absorb many times its own weight in liquid in order to store lower viscosity bodily exudates such as urine, menses, and/or runny or low viscosity feces. While the absorbent core may absorb the liquid that comes into contact with it, often any solid or highly viscous or particulate-containing material such as, for example, solid or pasty feces received by the absorbent article will typically remain at least partially on the topsheet, and in such instances may come into contact with the skin of a wearer of the absorbent article. It is well known that contact between skin and bodily exudates such as fecal matter may increase the occurrence of undesirable skin rashes or other ailments. BM (i.e., bodily exudate resulting from a bowel movement) or other bodily exudates that adhere or cling to the skin of a wearer will typically have to be cleaned off by the wearer of the absorbent article or a caregiver of the wearer. The removal of BM, for example, from skin may be an undesirable task for both wearers of absorbent articles and caregivers of the wearers. In light of this undesirability, some manufacturers of disposable absorbent articles have sought ways of isolating any BM contained in an absorbent article from the skin of the absorbent article wearer. Additionally, complete removal of feces from the skin is often difficult. Even when the previously soiled skin appears to be visually clean, micro-level contamination may remain on the skin and contribute to increased skin irritation.

One approach to isolating BM includes providing an absorbent article with an opening in the topsheet through which BM can pass to a more isolated portion of the absorbent article such as an interior portion proximate to the absorbent core. Once the BM passes through the opening, the topsheet may be configured to provide a barrier between the BM and the skin of the wearer. In some embodiments, the topsheet may be configured to have a hydrophilic side facing the wearer and a hydrophobic side facing the absorbent core of the article. The topsheet may be configured to have two hydrophobic sides, so that when bodily exudates pass from the wearer side of the topsheet to the absorbent core, they are inhibited or prevented from passing back from the absorbent core to the skin of the wearer. However, this approach may increase the complexity and/or the manufacturing cost a disposable absorbent article and may still leave a portion of the wearer's skin in contact with fecal material.

Another approach to the problem of BM on skin is to provide a barrier composition on the topsheet that repels or at least inhibits BM from sticking to the surface of the skin. For example, certain lotions and skin care compositions are known to at least reduce the tendency of BM to stick to the skin when they are applied to the surface of the skin. Such lotions and skin care compositions are typically hydrophilic or hydrophobic in nature. One drawback associated with the use of hydrophilic lotions on topsheets of absorbent articles is the phenomenon of over-hydration of the portion of skin in contact with the lotion. Over-hydration of the skin may lead to skin irritation and/or a wet skin feeling, and therefore may not provide a suitable option for BM isolation. Hydrophobic lotions, on the other hand, may provide at least some BM isolation and may not contribute significantly to skin over-hydration, but hydrophobic lotions may include other undesirable features such as interfering with the function of the topsheet, having a low washability (e.g., leaving an undesirable residue on the skin of the wearer), having a negative feel or appearance, and/or having insufficient skin cleaning ability. Thus, many manufacturers of absorbent articles desire a means of imparting hydrophobicity to a bodily surface without the negative aspects mentioned above.

Disposable cleaning articles for bodily surfaces may comprise one or more dry or wet-laid layers of a nonwoven material comprising synthetic or natural fibers adapted to remove contamination from skin, hair, or teeth. For example, facial tissues are typically wet-laid cellulosic webs adapted to remove nasal mucous or other waste from the skin, especially in the oral and nasal regions of the body. Toilet tissue is typically a wet-laid cellulosic web adapted to remove fecal material from a user's perianal region. Facial wipes may comprise a synthetic nonwoven web or foam material adapted to remove dirt, makeup, and other contamination from a user's facial region. One approach to increase the efficacy of disposable cleaning articles is to increase the basis weight of the article, which will typically increase the absorptive capacity of the article. While this may be at least partially effective for low viscosity contamination, highly viscous contaminants, visco-elastic contaminants, or contaminants having a high concentration of particulate matter may prove difficult to absorb regardless of the basis weight of the absorbent material. To deal with highly viscous contaminants, some providers of disposable cleaning article may increase the 3-dimensionality of the article, for example, by including depressions ridges, rugosities, and the like in order to provide storage capacity on the article surface for contaminants that are difficult to absorb. However, these approaches still may not be successful for highly adhesive or sticky contaminants, which tend to form a strong bond with a surface. One approach to reduce the adhesive or sticky properties of these kinds of contaminants is to disrupt the bond between the contaminant and the surface to which it is adhered. In some instances, this may be accomplished by using a liquid cleaning agent that includes, for example, water, a lotion, a silicone, and/or a surfactant. However, it may be difficult for the liquid cleaning aid to penetrate to the interface of the contaminant and the surface to which it is joined, and therefore the contaminant may not be removed even with a liquid cleaning aid. Another approach may be to include a beneficial composition that is releasably contained in a disposable cleaning article. For example, a hydrophobic skin care composition may be included in facial tissue and/or toilet tissue in order to reduce the likelihood of undesirable contamination of the skin, when the composition is applied to skin. While a hydrophobic skin care composition may provide the desired benefit of reducing the susceptibility of skin to the irritant effects of contamination, it is still subject to the same drawbacks described above with regard to disposable absorbent articles.

Disposable delivery articles may be adapted to transfer a beneficial substance or effect to the skin of a user and include facial wipes, moistening wipes, protective hand wipes, cleansing pads, tooth whitening articles, and heat wraps. These articles are generally effective at delivering the beneficial substance, but often lack the ability to protect the bodily surface from contaminants that may come into contact with the surface. Providing these articles with the ability to additionally facilitate the removal of undesirable contaminants via the establishment of a highly hydrophobic surface may be highly beneficial.

Existing in nature are surfaces that exhibit an inherent hydrophobicity (e.g., the surface of a lotus leaf). This phenomenon is sometimes referred to as super-hydrophobicity. The inherent hydrophobicity of certain natural surfaces may be due at least partially to hydrophobic nano- and/or microstructures provided on the surface by one or more naturally occurring hydrophobic materials. In some instances, the material may be produced naturally by an organism of which the surface is a part. In the case of the lotus leaf, the lotus plant produces and exudes a hydrophobic wax onto the surface of its leaves. The hydrophobic wax of the lotus plant has a surface that comprises hydrophobic micro and nano structures, which impart the inherent hydrophobicity to the lotus leaves. The micro and nano structured surface of the lotus leaf comprises a plurality of elevations and depressions wherein the heights of at least some the elevations and the distance between at least some of the elevations are on the order of nanometers, i.e., on a "nanoscale". When the material that includes the nanostructures is a hydrophobic material such as in the example of the lotus leaf, the relative spacing of the elevations may present a surface that water and other polar liquids are unable to penetrate or adhere to. In addition, when water or other similar liquids come into contact with such naturally hydrophobic surfaces, the water or other liquid may "roll off" of the hydrophobic surface and take any contamination with it. This phenomenon is sometimes referred to as the "Lotus Effect" and may result in a surface that is substantially self-cleaning when exposed to water. Nanostructures have been reproduced on some artificial surfaces through, for example, plasma etching, plasma polymerization, chemical vapor deposition, and surface coupling reactions. However, these methods are typically not suitable for use with certain biological surfaces such as skin.

Descriptions of the lotus effect and/or surfaces comprising nanostructures can be found in US2002/0150724A1 to Nun, et. al.; U.S. Pat. No. 6,660,363B1 to Barthlott; U.S. Pat. No. 5,500,216A to Julian, et. al.; U.S. Pat. No. 6,683,126B2 to Keller, et. al.; US2004/0014865A1 to Keller et. al.; US2003/0096083A1 to Morgan, et. al.; US2003/0124301A1 to Oles, et. al.; US2004/0154106A1 to Oles et. al.; EP1144536B1 to Reihs, et. al.; EP1144537B1 to Reihs, et. al.; EP1144733B1 to Reihs, et. al.; U.S. Pat. No. 6,787,585B2 to Rose, et. al.; US2004/0023824A1 to Zuechner, et. al.; and Biologie in Unserer Zeit, volume 28, Issue No. 5, pages 314-322, Barthlott, et. al.

Accordingly, it would be desirable to provide a disposable treatment article that transfers a composition for creating nanostructures on a bodily surface to the bodily surface during normal use of the article, wherein the nanostructures are capable of preventing, reducing, or resisting the adherence of contamination to the bodily surface. It would also be desirable to provide a nanostructure forming composition on a disposable treatment article that imparts good contamination resistance properties to skin and is not associated with skin over-hydration. It would further be desirable to provide a nanostructure forming composition on a disposable treatment article that renders a biological surface substantially hydrophobic.

SUMMARY OF THE INVENTION

In order to provide a solution to one or more of the problems described above, one embodiment discloses a disposable treatment article for contacting one or more bodily surfaces and increasing the contamination resistance of the bodily surfaces. The disposable treatment article comprises one or more substrates and an activatable nanostructure forming material. The nanostructure forming material is incorporated into one or more of the substrates. The nanostructure forming material is configured to provide hydrophobic nanostructures to a bodily surface when the activatable nanostructure forming material is activated and at least a portion of the nanostructure forming material is disposed on the bodily surface. The hydrophobic nanostructures comprise a plurality of nanoscale elevations and depressions. The nanostructure forming material, when activated and applied to the bodily surface reduces the adherence of a contaminant to the bodily surface.

Another embodiment discloses an article of commerce comprising a crushable nanoporous material adapted to form a plurality of nanostructures upon the application of between 6 N/m$^2$ and 7×10$^4$ N/m$^2$ of crushing pressure. The article also includes an applicator adapted to apply the nanoporous material to a bodily surface. The nanostructures reduce the adherence of a contaminant to the bodily surface when disposed on the bodily surface.

DETAILED DESCRIPTION OF THE INVENTION

Definitions

Figure 1:
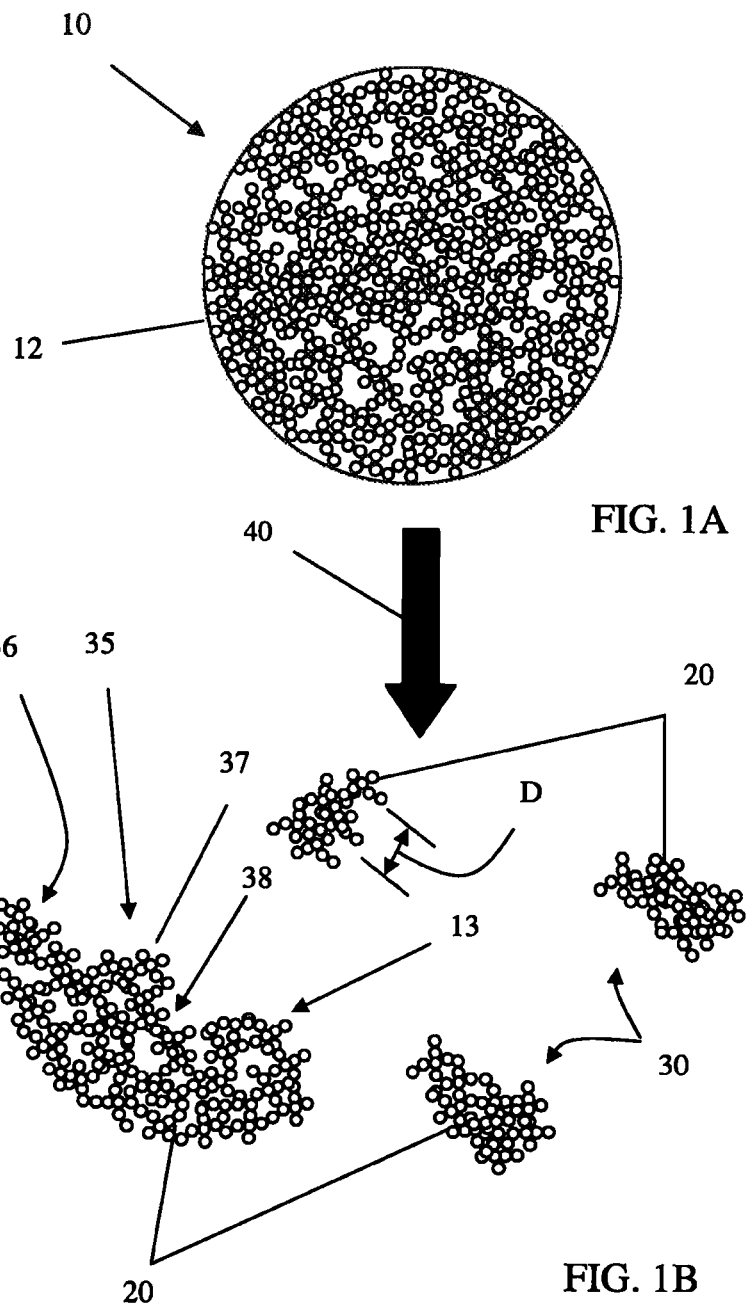
FIGS. 1A and 1B illustrate a nanostructure forming material being crushed.

"Adhere" refers to the ability of one material to cling or stick to another material and resist separation.

"Aerogel" refers to an extremely low density, porous solid formed by replacing the liquid of a gel with a gas. Typically, aerogels comprise silicon-, melamine-, or carbon-based materials, and exhibit densities in the range of 0.003 to 0.8 g/cm$^3$.

"Bodily surface" refers to a surface of the human body, including certain bodily cavities, that typically become contaminated through the course of normal daily activity. Non-limiting examples of bodily surfaces include skin, hair, fingernails, toenails, nostrils, tooth enamel, gums, the perianal region, the perineal region, mucous membranes (e.g., in the nasal cavity) and the like.

"Body contacting portion" or "body contacting" refers to a portion of an article that touches or is in liquid communication with a bodily surface during normal use of the article.

"Carrier" refers to a first material or composition that supports, holds, and/or localizes a second material or composition in order to facilitate transport of the second material from one location to another. For example, a lotion may support a nanostructure forming material, hold the nanostructure forming material on or in a disposable treatment article, and then transport the nanostructure forming material from the article to a bodily surface when the bodily surface contacts the lotion. Suitable examples of carriers are described in more detail herein below.

"Contaminant" or "contamination" refers herein to an undesirable or deleterious substance present on a bodily surface. Nonlimiting examples include urine, feces, menstrual fluid, mucous, grease, plaque, food residue, and the like.

"Crushing force" refers herein to a uni- or multi-directional force (uniform or variable) sufficient to cause at least a portion of the interior region of a nanostructure forming material to be exposed to the external environment, for example, by fracturing or breaking the nanostructure forming material into two or more nanoparticles, mesoparticles, and/or macroparticles.

"Crushing pressure" refers to the application of a crushing force over the area in which the force is applied.

"Depression" refers to a region of a material extending in the z-direction inward and away from the general plane of the material and which generally represents a concavity of the surface.

"Disposable treatment articles" ("DTAs") refers to articles generally not intended to be laundered or otherwise restored or reused (i.e., they are intended to be discarded after a single use and may be recycled, composted or otherwise discarded in an environmentally compatible manner).

"Disposed" generally means that an element(s) is formed (joined and positioned) in a particular place or position as a unitary structure with other elements or as a separate element joined to another element.

"Elevation" refers to a region of a material extending in the z-direction outward and away from the general plane of the material and which represents a convexity of the surface. While elevations generally extend outward and away from the surface upon which the nanostructure forming material is disposed, it is to be understood that a region of material characterized as an elevation may also include one or more smaller elevations and/or depressions in the same region. For example, a region of material may include a first elevation which extends 500 nm outward and away from the general plane of the material and one or more second elevations that extend 50 nm outward and away from the surface of the first elevation.

"Emulsion" refers to a mixture of two immiscible substances in which one substance (a dispersed phase) is dispersed in the other substance (the continuous phase).

"Hydrophilic," as used herein, refers to a material having a contact angle<90° according to The American Chemical Society Publication "Contact Angle, Wettability, and Adhesion," edited by Robert F. Gould and copyrighted in 1964.

"Hydrophobic," as used herein, refers to a material having a contact angle≥90° according to The American Chemical Society Publication "Contact Angle, Wettability, and Adhesion," edited by Robert F. Gould and copyrighted in 1964. In certain embodiments, materials comprising hydrophobic nanostructures may exhibit contact angles>120°, >140°, or even >150°.

"Joined" refers to configurations whereby an element is directly secured to another element by affixing the element directly to the other element and to configurations whereby an element is indirectly secured to another element by affixing the element to intermediate member(s) which in turn are affixed to the other element.

"Liquid communication" refers to the ability of a liquid to pass from one element of an article or system to a second element, for example, from the topsheet of a diaper to the absorbent core of the diaper. Such communication can result from direct physical contact between the two elements or can involve an intervening element. Elements of the present system can be said to be in liquid communication in the absence of a liquid, as long as such elements cooperate in such a way that when a liquid is present it is able to flow from one element to the other.

"Macroparticle" refers to a particle having a particle size greater than 1000 nanometers ("nm"). Macroparticles may be formed by aggregations of nanoparticles. For example, a macroparticle sized aerogel structure may be formed from an aggregation of nanoparticles.

"Mesoparticle" refers to a particle having a particle size ranging from 101 nm to 1000 nm.

"Nanoparticle" refers to a particle having a particle size ranging from 1 nm to 100 nm.

"Nanostructure" refers to a structure such as, for example, an elevation wherein the length of the structure in at least one dimension ranges from 1 nm to 100 nm, for example, from 1 nm to 50 nm, from 1 nm to 10 nm, or even from 1 to 5 nm. Surfaces comprising nanostructures are commonly referred to as "nanotextured." Nanotextured surfaces generally have nanostructures in at least one dimension (i.e., the thickness of the nanotextured surface is between 1 and 100 nm). In certain embodiments, a nanostructure may appear as a nanoscale element on a macroscopic surface (i.e., the element has at least one dimension from 1 nm to 100 nm). In such an embodiment, the element may be 1, 2, or 3 dimensional, with one or more of the dimensions being nanoscale. In certain embodiments, nanostructures may comprise a plurality of elevations and depressions disposed on the surface of a particle or particle fragment. In certain embodiments, the maximum distance between any two adjacent nanostructures may be less than 100 nm, but need not necessarily be so. The examples, figures, and written description provided herein below further define what is meant by nanostructure.

"Nanostructure Forming Material" (NFM or NFMs) refers to a material or composition that forms a plurality of structures with nanoscale topography on a substrate when the NFM is applied to the substrate. The NFM may be activatable, or the NFM may provide nanostructures without activation. Activatable NFMs generally utilize an activation stimulus or stimuli such as, for example, a suitable amount of crushing pressure in order to provide a desired amount of nanostructures for achieving an anti-contamination benefit. Other examples of activatable NFMs are described in more detail hereinbelow. An NFM may be applied to a substrate as a liquid, suspension, emulsion, mixture, or solid. A hydrophobic or hydrophilic NFM is an NFM having surface groups which are inherently hydrophobic or hydrophilic, respectively.

"Particle" refers to a relatively small piece of solid substance (e.g., having a longest dimension between 1 nm and 10 mm). Suitable nonlimiting forms of particles include granules, pulverulents, spheres, aggregates, agglomerates, combinations thereof and the like. Particles may have any shape or combination of shapes such as, for example, cubic; rod-like; polyhedral; spherical; rounded; angular; irregular; randomly-sized irregular shapes (i.e., pulverulent products of a grinding or pulverizing step). Particles may be organic, inorganic, or any combination thereof. While certain embodiments described herein describe NFMs in the form of particles, it is to be understood that NFMs comprising shapes such as needle-like, flake-like, or fiber-like are also contemplated herein.

"Shearing force" refers to a force that causes or tends to cause two regions of the same material to slide relative to each other in a direction parallel to the applied force vector.

"Skin Care Composition" refers to any composition that includes one or more agents that, when transferred from an article to a wearer's skin, provide a therapeutic and/or protective skin benefit such as, for example, a lotion. Suitable examples of skin compositions can be found in U.S. Pat. No. 5,607,760 to Roe; U.S. Pat. No. 5,609,587 to Roe; U.S. Pat. No. 5,635,191 to Roe, et al.; U.S. Pat. No. 5,643,588 to Roe, et al.; and U.S. Pat. No. 6,217,890 to Paul, et al.

"Colloidal suspension" refers to a colloidal solid suspended in a liquid where the liquid is the continuous phase. The colloidal suspension may be prepared by any suitable process commonly known in the art, such as a dispersion or condensation process (i.e., precipitation) or sol-gel process. The colloidal suspension may be adapted to provide a nano-structure forming material, for example, by depositing the suspension on a substrate to form a film (e.g., by dip-coating or spin-coating), casting the suspension into a suitable container with the desired shape (e.g., to obtain a monolithic ceramics, glasses, fibers, membranes, aerogels), or used the suspension to synthesize powders (e.g., microspheres, nanospheres).

"Wetting" generally refers to the interaction between a fluid and a surface, when the two are brought into contact. When a liquid has a high surface tension (strong internal bonds), it may form a droplet, whereas a liquid with low surface tension tends to spread out over an area (wetting the surface). If a surface has a high surface energy (or surface tension), a droplet may spread, or wet, the surface, but if the surface has a low surface energy, a droplet may form. This phenomenon is generally attributed to the minimization of interfacial energy between the fluid and the surface.

"Xerogel" refers to a material formed from a colloidal suspension by drying with unhindered shrinkage (e.g. 90%) and may be analogized to drying a gelatin. Xerogels are generally understood to be what remains when the liquid part of an alcogel is removed by evaporation, or similar methods. Xerogels typically retain high porosity (e.g., 25%) and high surface area (e.g., 150-900 $m^2/g$), along with a relatively small pore size (e.g., 1-10 nm). In certain embodiments, a Xerogel may be configured as a film that is subsequently broken/pulverized/ground to create particles that have nanostructured surfaces. Examples of suitable Xerogels for use herein include xerogels that retain their shape, size, and/or geometry in dry and wet conditions. An "alcogel" is a mixture that, at the gel point, forms a rigid substance (the alcogel). The alcogel can typically be removed from its original container and can stand on its own. An alcogel typically consists of two parts, a solid part and a liquid part. The solid part is formed by a three-dimensional network of linked particles such as, for example, oxide particles. The liquid part (the original solvent of the Sol) fills the free space surrounding the solid part. The liquid and solid parts of an alcogel occupy the same apparent volume.

Disposable Treatment Article

Current DTAs may be perceived by some consumers as providing bodily surfaces with little or no resistance to contamination. In instances where a DTA is perceived as providing at least some resistance to contamination, the DTA may have other properties that the consumer finds undesirable, for example, over-hydration of the skin. Surprisingly, it has been found that by including one or more hydrophobic nanostructure forming materials ("NFMs") in a DTA, a hydrophobic layer of nanostructures may be provided on a bodily surface. The nanostructured layer may function much like an anti-adhesion barrier to a variety of contaminants such as, for example, BM and thereby make it more difficult for a particular contaminant(s) to adhere to the bodily surface. In this manner, a DTA for cleaning and/or contacting a bodily surface may be adapted to provide the bodily surface with at least some resistance to contamination while avoiding at least some of the undesired properties of other DTAs.

Bodily surfaces of interest for use with the DTAs described herein include those that are at least occasionally exposed to the external environment and contaminants. Common contaminants include, without limitation, human biological material such as blood, exfoliated skin cells, bodily exudates (e.g., feces, urine, menses, nasal or tracheal mucous, sweat, and sebum), bacteria, bacterial excretions, dirt, grease, paint, foods, makeup, plaque, combinations thereof and the like. The bodily surface may be relatively continuously exposed, directly or indirectly, to the environment or may be an occluded or enclosed region that is only intermittently exposed.

DTAs suitable for use herein include any disposable article intended to contact or clean one or more bodily surfaces such as skin, teeth and/or hair. Nonlimiting examples of DTAs include: diapers, diaper inserts, training pants, adult incontinence articles, sanitary napkins, pantyliners, wipes, toilet tissue, paper towels, napkins, facial tissue, disposable teeth cleaning devices, disposable hair cleaning devices, combinations thereof, and the like. Suitable examples of DTAs, configurations of DTAs, and methods of making DTAs are described in U.S. Pat. No. 3,860,003 to Buell; U.S. Pat. No.

5,151,092 to Buell, et al.; U.S. Pat. No. 5,221,274 Buell, et al.; U.S. Pat. No. 5,554,145 to Roe et al.; U.S. Pat. No. 5,569,234 to Buell et al.; U.S. Pat. No. 5,580,411 to Nease et al.; U.S. Pat. No. 6,004,306 to Robles, et al. Suitable examples of wipes are described in U.S. Pat. No. 6,808,791 to Curro, et al.; U.S. Pat. No. 6,706,028 to Roe, et al.; U.S. Pat. No. 6,986,932 to Zink, et al.; U.S. Pub. Nos. 20050227563 to Bond; 20040242097 to Hasenoehrl, et al.; and 20040265533 to Hoying, et al. Suitable examples of paper towels are described in U.S. Pat. No. 5,893,965 to Trokhan, et al. Suitable examples of toilet tissue are described in U.S. Pat. No. 5,716,692 to Warner, et al.

The DTAs suitable for use herein may include a substrate of any suitable material commonly known in the art such as, for example, nonwovens, films of polyolefin, foams, elastomers, or cellulosic materials. The substrate may include one or more compositions to aid a user in the particular task(s) for which the DTA is suited. For example, a wipe may include a lotion or soap composition while a treatment article for cleaning teeth may comprise an abrasive, breath freshening, or whitening composition. The beneficial composition may be disposed on one or more surfaces of the treatment article or the composition may be impregnated in the substrate of the treatment article. The DTA may include one or more hydrophobic NFMs. The NFMs may be disposed on or in the DTA in any suitable location, for example, on one or more surfaces of the DTA that typically contact a bodily surface when the article is used as intended. The NFM may be secured to the DTA by any suitable means commonly known in the art such as, for example, by electrostatic forces, van der Waals forces, mechanical forces, entrapment, embedding, magnetic forces, adhesive forces, combinations thereof, and the like. In a particularly suitable embodiment, the NFM may be suspended in one or more carriers or beneficial compositions that are disposed on a disposable diaper. An exemplary disposable diaper may include a wearer-facing topsheet, a garment-facing backsheet, an absorbent core, one or more leg cuffs, and a hydrophobic skin care composition coated on one or more portions of the topsheet and/or leg cuffs. The skin care composition in this example may act as a matrix for carrying an NFM, and when the diaper is placed on a wearer, the topsheet, which typically contacts the skin of the wearer during use, may act as an applicator for applying the skin care composition and the NFM to the wearer's skin. In certain embodiments, at least a portion of the carrier may evaporate leaving the NFM on the topsheet where it may be available to contact and transfer to the wearer's skin. In certain embodiments, a disposable wet-wipe, which typically comprises a fibrous substrate and a liquid benefit composition, may be adapted to apply and deposit an NFM on the skin of a user of the wet-wipe. In such an embodiment, the liquid benefit composition such as, for example, an aqueous cleaning composition may act as a matrix for carrying the NFM.

The DTA may be any suitable wet-laid or air-laid, through-air-dried (TAD) or conventionally dried, creped or uncreped fibrous structure. In certain embodiments, the fibrous structures of the present invention mat be disposable. For example, the fibrous structures of the present invention are non-textile fibrous structures. In certain embodiments, the fibrous structures of the present invention are flushable, such as toilet tissue.

Nonlimiting examples of processes for making fibrous structures include known wet-laid papermaking processes and air-laid papermaking processes. Such processes typically include the steps of preparing a fibrous element composition such as a fiber composition, in the form of a suspension in a medium, either wet, more specifically an aqueous medium (e.g., water), or dry, more specifically a gaseous medium (e.g., air). The suspension of fibers within an aqueous medium is oftentimes referred to as a fiber slurry. The fibrous element suspension is then used to deposit a plurality of fibrous elements onto a forming wire or belt, in the case of a wet-laid process, and a collection device or belt, in the case of an air-laid process. Further processing of the fibrous structure may be carried out such that a finished fibrous structure is formed. For example, in typical papermaking processes, the finished fibrous structure is the fibrous structure that is wound on the reel at the end of papermaking. The finished fibrous structure may subsequently be converted into a finished product (e.g., a sanitary tissue product). The fibrous structure may be subjected to one or more converting operations such as embossing, tuft-generating, thermal bonding and calendaring. The NFM may be deposited onto the fibrous structure at any point during the making and/or converting process(es) of the fibrous structure. In addition, the NFM may be included in the fibrous slurry used to form the fibrous structure. In certain embodiments, the NFM may be included in a surface treating composition such as a surface softening composition and/or lotion composition, which is applied to a surface of the fibrous structure, for example, by way of transfer from a drying belt and/or Yankee dryer during the fibrous structure making process. In certain embodiments, the NFM may be printed onto a surface of the fibrous structure, for example, with a gravure roll. The NFM may also be sprayed onto a surface of the fibrous structure, for example, by an ink-jet printing process. The NFM may even be extruded onto a surface of the fibrous structure.

The fibrous structure may be made up of fibers and/or filaments. Non-limiting examples of filaments include melt-blown and/or spunbond filaments. Non-limiting examples of polymers that can be spun into filaments include natural polymers such as starch, starch derivatives, cellulose (e.g., rayon and/or lyocell), and cellulose derivatives (e.g., hemicellulose and hemicellulose derivatives) and synthetic polymers including, but not limited to, thermoplastic polymer filaments such as polyesters, nylons, polyolefins (e.g., polypropylene filaments, and polyethylene filaments), and biodegradable thermoplastic fibers such as polylactic acid filaments, polyhydroxyalkanoate filaments, polyesteramide filaments and polycaprolactone filaments.

The fibers may be naturally occurring fibers, which means they are obtained from a naturally occurring source such as a vegetative source (e.g., trees and/or plants). Such fibers are typically used in papermaking and are oftentimes referred to as papermaking fibers. Papermaking fibers useful in the present invention include cellulosic fibers commonly known as wood pulp fibers. Applicable wood pulps include chemical pulps such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the DTAs of the present invention are fibers derived from recycled paper.

In addition to the various wood pulp fibers, other cellulosic fibers such as cotton linters, trichomes, rayon, lyocell and bagasse fibers can be used in the fibrous structures of the present invention.

In addition to being useful as toilet tissue, facial tissue, paper towels and wipes, the DTAs may also be useful for treating hard surfaces such as hardwood flooring and/or linoleum, furniture wipes, glass wipes, all-purpose wipes, fitness equipment wipes, jewelry wipes, disinfecting wipes, automotive wipes, appliance wipes, toilet, tub and sink wipes and even preventive toxin wipes such as poison ivy/poison oak wipes.

Carrier

In certain embodiments, it may be desirable to incorporate a carrier into a DTA to facilitate the transfer and/or contact of an NFM to a bodily surface. NFMs are described in more detail hereinbelow. By "incorporate" it is generally meant herein that the carrier becomes an integral element of the DTA. The carrier may be incorporated into a DTA by any suitable means or pattern commonly known in the art. In certain embodiments, the carrier may be applied to the surface(s) of one or more elements of the DTA, such as a topsheet or leg cuff, by any means commonly known in the art including, without limitation, slot coating, extruding, dipping, spraying, and the like. Nonlimiting examples of suitable patterns include full coverage, stripes, spirals, and a plurality of regular or irregular shapes on one or more of the article surfaces. The carrier may be incorporated into one or more individual DTA elements or portions of elements at any point in the assembly process of the DTA. Alternatively or additionally, the carrier may be incorporated into one or more individual DTA elements during or subsequent to the formation of the elements but prior to the element entering the assembly process of the DTA. In certain embodiments, the carrier may be applied to a nonwoven web after formation of the web, but prior to the web being shipped to a manufacturer of DTAs. In certain embodiments, individual fibers may be exposed to the carrier and subsequently formed into a fibrous substrate for use as an element in a DTA. In certain embodiments, the carrier may be impregnated in the fibers of the DTA, for example, by including the carrier in a thermoplastic melt composition (e.g., polypropylene) prior to or during a fiber forming process involving the thermoplastic composition such as, for example, a spunbonding or meltblowing process. The carrier and the thermoplastic composition may be selected or adapted such that when fibers are formed from the thermoplastic composition at least a portion of the carrier and the NFM suspended in the carrier migrate to the surface of the fiber. In this way, a DTA that includes such fibers may be configured to contact the fibers, and hence the carrier, to the skin of a user of the DTA. In certain embodiments, the carrier may be incorporated into the DTA as a liquid, but become a solid or semi-solid subsequent to such incorporation. For example, the carrier may be applied to the DTA as a liquid at a first elevated temperature and then cooled to a second temperature at which the carrier solidifies or partially solidifies.

In certain embodiments, the carrier may encase the NFM and/or may hold the NFM at or near a surface of the carrier. The NFM may be included in the carrier prior to, during, or subsequent to incorporating the carrier into a DTA. In certain embodiments, the NFM may be applied to the carrier subsequent to the application of the carrier to the DTA such as when the carrier is in a liquid or semi-solid state. In such an embodiment, the NFM may be held in place as the carrier cools and/or hardens. In certain embodiments, the carrier may include one or more volatile components that at least partially evaporate subsequent to the suspension of the NFM in the carrier and/or incorporation of the NFM-containing carrier into a DTA. The NFM may be selected or adapted such that once the volatile component(s) evaporates or partially evaporates, the NFM adheres to a predetermined portion of the DTA where, ideally, it will contact a bodily surface.

Carriers incorporated into a DTA, as described herein, may be selected or adapted to at least partially transfer to a bodily surface upon normal use of the DTA, or to remain on the DTA, as desired. It may be desirable to provide a carrier that performs one or more secondary functions. Nonlimiting examples of secondary functions include providing skin protection and/or a therapeutic benefit; increasing the cleaning or absorbing ability of a DTA; reducing the friction between the DTA and a bodily surface contacted by the DTA, combinations of these and the like.

While a carrier may be used as described above, it is to be understood that embodiments where the NFM is held on or within the DTA, or an element thereof, without the use of a carrier are also contemplated herein. For example, particles of the NFM may be entrapped in a fibrous matrix such as a nonwoven or highloft material, or within a laminate structure having a fibrous or porous surface. Exemplary laminate structures include two or more layers of material joined together to form a layered structure wherein the NFM is disposed on one or more of the layers and/or between one or more of the layers. Laminate structures may be joined together by any suitable means known in the art such as, for example, by adhesives, patterned adhesives, mechanical bonding, and ultrasonic bonding. The NFM may be disposed in the laminate as a fugitive composition (i.e., unbound or loosely bound such that the NFM is free to migrate throughout at least a portion of article or a layer of the article). In certain embodiments, the NFM may be joined to a particular element or layer of a DTA with an adhesive or other suitable joining means.

In embodiments comprising a laminate structure, it may be desirable to configure the DTA and the NFM such that the NFM is brought into contact with a bodily surface during normal use of the DTA. Upon contact the NFM may be selected or adapted to break apart with the application of a suitable force and/or pressure such as, for example, a suitable crushing pressure prior to or during the use of the DTA by a user. At least some of the resulting activated particles may be small enough to pass out of the fibrous or laminate structure and adhere to a bodily surface contacted by the DTA. The laminate may have a first surface oriented toward the user's skin and a second surface oriented away from the user's skin. The first and second surfaces may have different porosities. In such embodiments, the first surface may have a higher porosity than the second surface. Additionally or alternatively, the pore or opening size in the first surface may be smaller than the unactivated (e.g., uncrushed) NFM particles or macroparticles to prevent migration or loss of the NFM prior to use. Further, the pore size in the first surface may be configured to be larger than activated mesoparticles or nanoparticles such that the activated particles may transfer to a bodily surface and form a nanostructured layer thereon. In certain embodiments, the NFM may be held within the void spaces in a highloft material or other three-dimensional porous layer until the NFM is otherwise released to contact the skin of the user. Regardless of the number, porosity or other characteristics of the laminate layers, the NFM may be held in one or more layers by any particle-retention means known in the art. An NFM-containing laminate or three-dimensional structure may also include a carrier as described herein. In certain embodiments, the NFM may be held under an impermeable protective layer such as a film and released to the bodily surface via an additional step such as removing or peeling away the protective layer, or via contact with water (e.g., where the protective layer is water soluble). In certain embodiments, an extensible or elastic protective layer may comprise openings sufficiently small to prevent the NFM or partially activated NFM particles from escaping, but upon extension or stretching of the protective layer, the openings become sufficiently large to enable the NFM or activated NFM to pass through to the bodily surface.

Nanostructure Forming Material

NFMs suitable for use with the DTAs disclosed herein may comprise a variety of shapes, compositions, particle sizes, and/or structural configurations. Particularly suitable NFMs include, without limitation, crushable nanoporous materials such as aerogels; aerogel-like materials (i.e., 3D, nanoporous, and including at least 90% air, by volume of the NFM); and xerogel or xerogel-like materials (i.e., more condensed nanoporous structure compared to aerogels). In certain embodiments, the NFM may be configured as a crushable aerogel comprising silicas such as pyrogenic silicas, precipitated silicas, and doped silicates; aluminum oxides; silicon dioxides; pulverulent polymers; $Mg(OH)_2$; boehmite $(Al(O)OH)$; hydroxyapatite; bentonite; hectorite; combinations thereof and the like.

Other NFMs include organic compositions and structures. Examples of organic NFM structures include templated nanocomposite thin films, lamellar, hexagonal cylinders; bicontinuous cubic, body-centered cubic spheres; and/or biological nanostructures. Examples of organic NFM compositions include, without limitation, dendrimers; silicone resins and silicone containing polymeric material such as silicone polyethers, silicone quaternary compounds, silicone amines, silicone phosphates, silicone betaines, silicone amine oxides, alkylated silicones, alkylated silicones, fluorinated silicones, alkylated silicone polyethers, silicone polyether esters and carboxylates and reactive silicones (polyalcohols, isocyanates, acrylates, vinyls and epoxides); and block copolymers (e.g., AB diblock, cyclic AB diblock, ABC triblock, ABA triblock, ABC star block, $AB_n$ comb, $(AB)_n$ star, $(AB)_n$ multiblock).

The NFMs disclosed herein may be naturally hydrophobic or hydrophilic or modified to be hydrophobic or hydrophilic, for example, by treating the NFM with a composition comprising alkylsilanes, fluoroalkylsilanes, and/or disilazanes.

Suitable NFMs for use with DTAs as disclosed herein generally include materials that provide nanostructures on a bodily surface when applied to the bodily surface. When an NFM is contacted with a bodily surface, it may be desirable to select and/or adapt the NFM to remain on the bodily surface in order to provide an extended benefit such as an extended anti-contamination benefit. Suitable NFMs may include macro or mesoparticles having an average particle size on the order of millimeters, micrometers or even nanometers such as, for example, between 1 mm and 500 µm, between 499 µm and 500 nm, or even less than 500 nm. In certain embodiments, the NFM may comprise a nanoporous material having an average particle size of about 1 mm (e.g., ±25%). The nanoporous material may be thought of as a particle having a honeycomb-like structure (i.e., a particle having relatively large open areas dispersed throughout the particle). One or more portions of the interior or exterior surface of the NFM may include nanostructures. Alternatively or additionally, the NFM may be activatable. The term "activatable" (and variations thereof) means the NFM requires an external stimulus or stimuli such as, for example, a crushing pressure, a shearing force, and/or drying before the desired nanostructures are provided. Activatable NFMs are exemplified below. The external stimulus or stimuli may be provided by a user of the DTA and/or from sources present in the environment to which the NFM is exposed. In certain embodiments, an NFM may be selected and/or adapted to desirably interact with one or more of the compositions typically associated with a bodily surface (e.g., naturally occurring oils and/or bacteria found on the skin, hair, and/or teeth of a user). In this way, the NFM may be joined to the bodily surface through surface interactions between the NFM and the compositions present on the bodily surface. In certain embodiments, the NFM may be selected and/or adapted to remain on a particular bodily surface through the action of an electrostatic force between the NFM and the bodily surface. In certain embodiments, the NFM may be selected and/or adapted to remain on a particular bodily surface through the action of van der Waals forces between the NFM and the bodily surface.

In certain embodiments, an NFM may provide contamination resistance to one or more portions of a DTA. For example, an NFM disposed on the topsheet and/or other element of a diaper may increase the resistance of at least a portion of the topsheet and/or other element to contamination in the same or a similar manner as the NFM increases the contamination resistance of a bodily surface. In this example, a diaper topsheet or portion thereof that includes an activated NFM may become resistant to fecal adhesion. Thus, feces deposited into the diaper by a wearer may be more easily removed, for example, by dumping at least some, and ideally all, of the feces from the diaper into a toilet or other appropriate disposal receptacle. Placing the feces from a diaper into an established sewage system, which is typically configured to handle such waste, may reduce or even eliminate potential pathogen-containing feces from entering a landfill or other conventional waste disposal system. Additionally or alternatively, placing the feces from the diaper into an appropriate disposable receptacle such as a trash bin may provide an opportunity to at least recycle or compost reusable and/or biodegradable portions of the diaper.

FIGS. 1A and 1B show an example of an activatable NFM 10 that may be activated by an activation stimulus 40. Prior to being subjected to the activation stimulus 40, the NFM 10 may include few or even no nanostructures 30 on its surface 12, as shown in FIG. 1A. However, when subjected to a suitable activation stimulus 40 (e.g., a shearing and/or crushing force of between 0.1 N and 5 N or a crushing pressure of between 6.9 $N/m^2$ and 6.9×$10^4$ $N/m^2$), the NFM 10 may separate into two or more smaller fragments 20, as shown in FIG. 1B. The fragments 20 may include a plurality of nanostructures 30 on one or more surfaces. The fragments 20 may comprise nanoparticles that resist further crushing (i.e., exhibit minimal or no further reduction in particle size) and/or the fragments 20 may comprise macroparticles and/or mesoparticles. Macroparticles and mesoparticles, when present, may continue to decrease in size, upon the application of additional activation stimulus or stimuli 40 or the continued application of the same activation stimulus 40, until a desired particle size, surface area, or morphology is achieved. Suitable examples of activation stimuli include crushing and/or shearing forces/pressures applied to the NFM by a user; a pH or pH range; a temperature or temperature range; enzymes; bacteria; bacteria exudates; water; oils; minerals; bodily exudates; compositions typically found in bodily exudates; other compositions typically found on a bodily surface; and combinations of these. The macroparticles and/or mesoparticles, when present, may separate into smaller particles upon exposure to, for example, an enzyme and/or other composition present on a bodily surface. Fragments 20 having particle sizes of less than 10%, 1%, 0.1% or even 0.01% of the original NFM 10 particle size may be suitable for providing the desired nanostructures. Crushing one or more of the fragments 20 exposes at least one surface 13 that includes nanostructures 30 that were not exposed prior to activation. The nanostructures 30 may comprise elevations 35 and depressions 36. The nanostructures 30 may range in height from 1 nm to 1000 nm. The height of an elevation 35 is measured as the distance from the tip 37 of the elevation 35 to the bottom 38 of an adjacent depression 36. When the nanostructure includes multiple adjacent depressions 36 that yield different heights, the height is calculated using the depression 36 that yields the greatest distance. The distance D between any two adjacent elevations may range from 1 nm to 1000 nm.

The stimulus required to activate an activatable NFM may vary, depending on the shape, composition, particle size, carrier, and/or structural configuration of the NFM. In certain embodiments, it may be desirable to configure an NFM to require a relatively low force and/or pressure to activate the NFM (e.g., less than 5 N, 3 N, 0.5 N, or 0.1N of crushing and/or shear force, and/or less than $7\times10$ N/m$^2$, $3\times10^4$ N/m$^2$, $1\times10^3$ N/m$^2$, or 6 N/m$^2$ of crushing pressure). It is believed, without being limited by theory, that decreasing the amount of stimulus (e.g., force or pressure) needed to crush an NFM increases the probability that the NFM will be activated when brought into contact with a bodily surface of a user during a typical usage of the NFM-containing article, ideally, without any additional action on the part of a user. An NFM that is activated by relatively low crushing force may be desirable for use on the topsheet of a disposable absorbent article such as a diaper. In such an embodiment, the anti-contamination benefit of the NFM may be conferred to a wearer of the diaper with little or no action on the part of a caregiver of the wearer beyond placing the diaper on the wearer and/or the subsequent wearing process of the diaper.

In certain embodiments, it may be desirable to use an NFM that is activated by a relatively high force (e.g., greater than 5 N) and/or crushing pressure (e.g., greater than $7\times10^4$ N/m$^2$) in order to reduce the likelihood of undesirably activating the NFM prior to the intended use of a DTA into which the NFM is incorporated. In one particularly suitable example, an NFM that is at least partially activated by the force(s) exerted on the NFM during normal use of the diaper (e.g., when the wearer walks, crawls, sits, and/or rolls over) may be incorporated into the topsheet of a disposable diaper. In certain embodiments, it may be desirable to use an NFM that is activated by a relatively high activation force and/or pressure for incorporation into a wipe. Often wipes are stored in containers that are configured to dispense the wipes one at a time, and it is not uncommon for the wipe to be subjected to a variety of forces and/or pressures during the dispensing process. Incorporating a high-activation force/pressure NFM into a wipe may increase the likelihood that the NFM will not be undesirably activated during the dispensing process, and/or during routine handling of the wipe. In certain embodiments, it may be desirable to select and/or adapt an NFM to be activated by a relatively high crushing force/pressure in order to provide an NFM that is substantially activated only after contacting and adhering to a bodily surface such as in the use of a facial tissue, toilet tissue or other similar cleaning article.

In certain embodiments, it may be desirable to include one or more NFMs that are activated by two or more different forces, pressure, and/or other stimuli. For example, two NFMs that are activatable by two different amounts of crushing force/pressure may be incorporated into a wipes product such as a baby wipe. The first NFM may be selected and/or adapted to be activatable by a relatively low force/pressure, while the second NFM is activatable by a relatively high force/pressure. In this example, the first NFM may be substantially activated when the wipe is dispensed from a container, and the second NFM may remain substantially unactivated. Upon application of a suitable force/pressure to the wipe by a user, the second NFM may be activated. In another example, a first NFM that is activatable by the application of a relatively low activation force/pressure and a second NFM that is activatable by the application of a relatively high activation force/pressure may be incorporated into a wipes product such as a baby wipe. In this example, the first NFM may provide nanostructures on a first bodily surface such as the hands of a caregiver or other user, while the second NFM provides nanostructures on a second bodily surface such as the buttocks of a child being cleaned with the baby wipe. Continuing with this example, the nanostructures formed from activating the first NFM may provide a moisturizing benefit to the hands of a caregiver, while the nanostructures formed by activating the second NFM may provide an anti-contamination benefit to the skin of the child being cleaned with the wipe. In certain embodiments, a first NFM and a second NFM may be activated by different mechanisms. For example, the first NFM may be activated by a crushing force/pressure and the second NFM may be activated by contact with an activating agent such as water or an enzyme.

In certain embodiments, it may be desirable to arrange nanostructures on a bodily surface in a substantially continuous layer, thereby providing substantially continuous surface coverage of the bodily surface. A bodily surface that is substantially covered with nanostructures may exhibit a particularly suitable degree of contamination resistance as a result of the lotus effect provided by the nanostructures. The layer of nanostructures may have a thickness of about 100 to 200 nm. It is believed, without being limited by theory, that thickness may not affect the contamination resistance phenomena of the surface. However, the thickness of the nanostructure layer may affect the durability of the contamination resistance phenomenon. For example, a thicker layer may provide contamination resistance for a longer period time than thinner layer. The thickness of the layer may also impact the aesthetics of the DTA or the surface on which the nanostructure layer is disposed. It is further believed, without being limited by theory, that the nanoscale dimensions of the nanostructures, especially when the nanostructures are arranged in a substantially continuous layer or film, may inhibit or even prevent polar and non-polar liquids such as water and oils from wetting the bodily surface upon which the layer of nanostructures is disposed. When the nanostructures comprise a hydrophobic material, the nanostructures may present a surface that repels polar liquids to the extent that polar liquids will generally attempt to move away from the hydrophobic nanostructures, for example, by forming spherical shapes and rolling off of the nanostructure layer.

Figure 2:
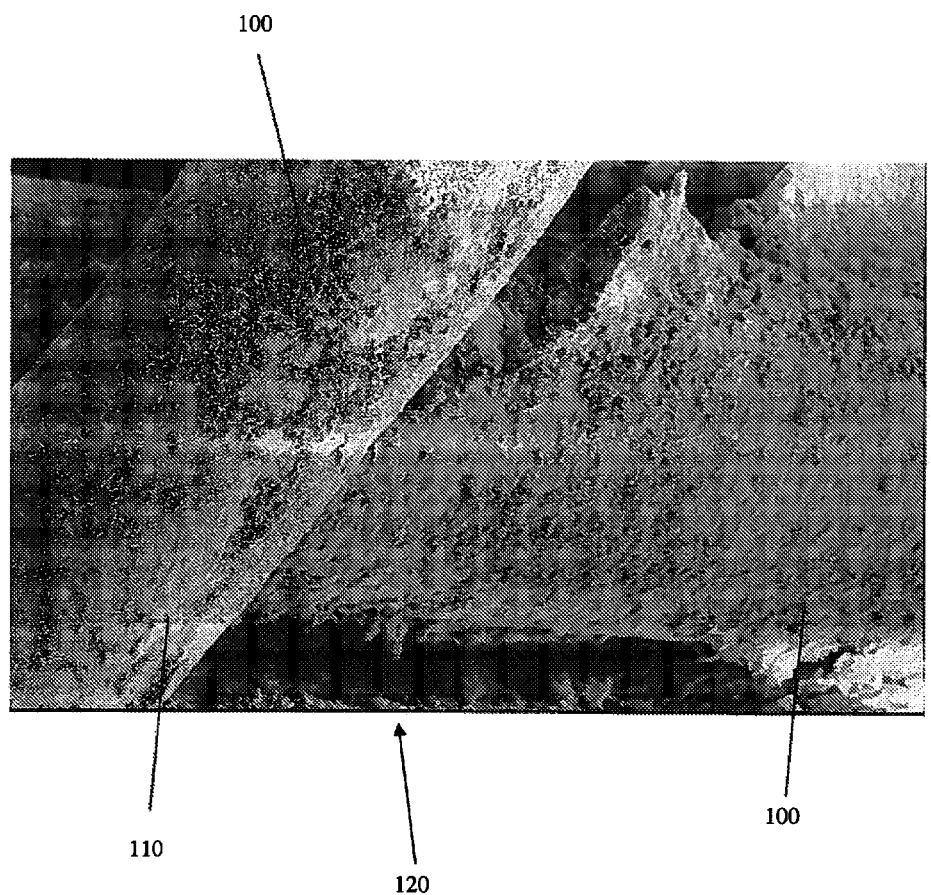
FIGS. 2 and 3 are representations of SEM micrographs of a nanostructure forming material disposed on a fibrous substrate.
Figure 3:
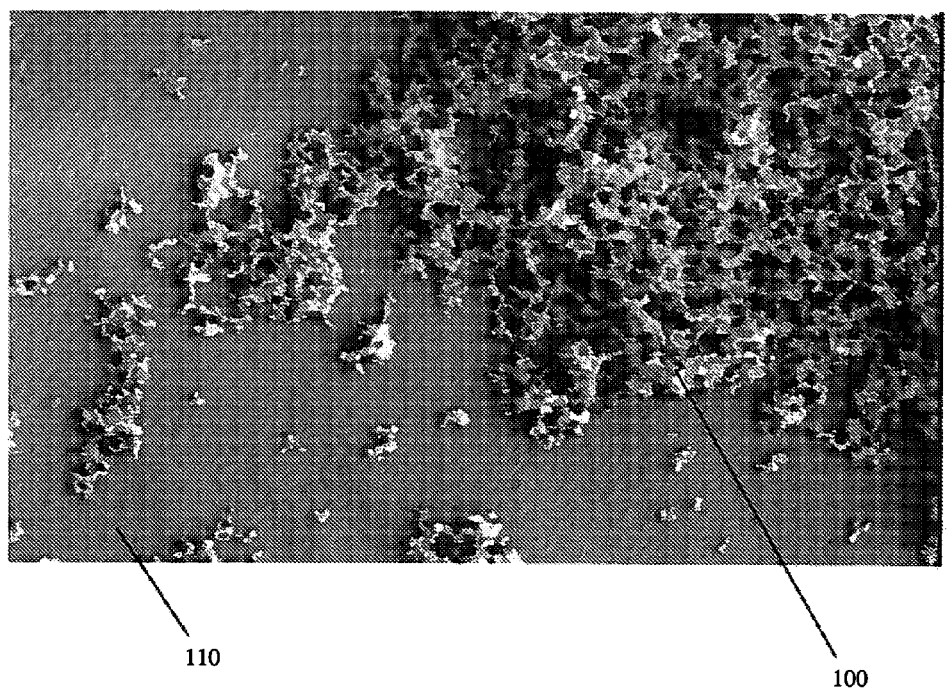

FIG. 2 shows a Scanning Electron Microscopy ("SEM") micrograph of an NFM 100 disposed on a fiber 110 of a nonwoven substrate 120. FIG. 3 shows a 10× magnification of the fiber 110 from FIG. 2. The NFM 100 may be dispersed in a solvent to form a dispersion and applied to the nonwoven substrate 120. The solvent may then be dried leaving a substantially continuous layer of NFM 100 on one or more portions of at least some of the fibers 110. Nonlimiting examples of suitable solvents include water, cyclomethicone, ethylacetate, ethyl alcohol, isopropol alcohol, isohexadecane, and pentamethyl propane. One or more dispersant(s)/additive(s) may be included in the dispersion, as desired. The dispersant and/or NFM may also comprise a polymer. In certain embodiments, the dispersion may include aggregates of hydrophobic NFMs 100 that have a size distribution ranging from greater than 100 mm to 1 mm. Aggregate sizes in a suspension or emulsion may be further controlled by ultrasonication, solvent choice, and/or concentration of solid. In certain embodiments, the NFM 100 may include an aggregate of hydrophobic silica nanoparticles delivered to the nonwoven substrate 120 from a solvent of cyclomethicone. One particularly suitable example of hydrophobic silica includes AEROXIDE LE1 brand hydrophobic silica available from Degussa AG, Duesseldorf, Germany.

Figure 4A:
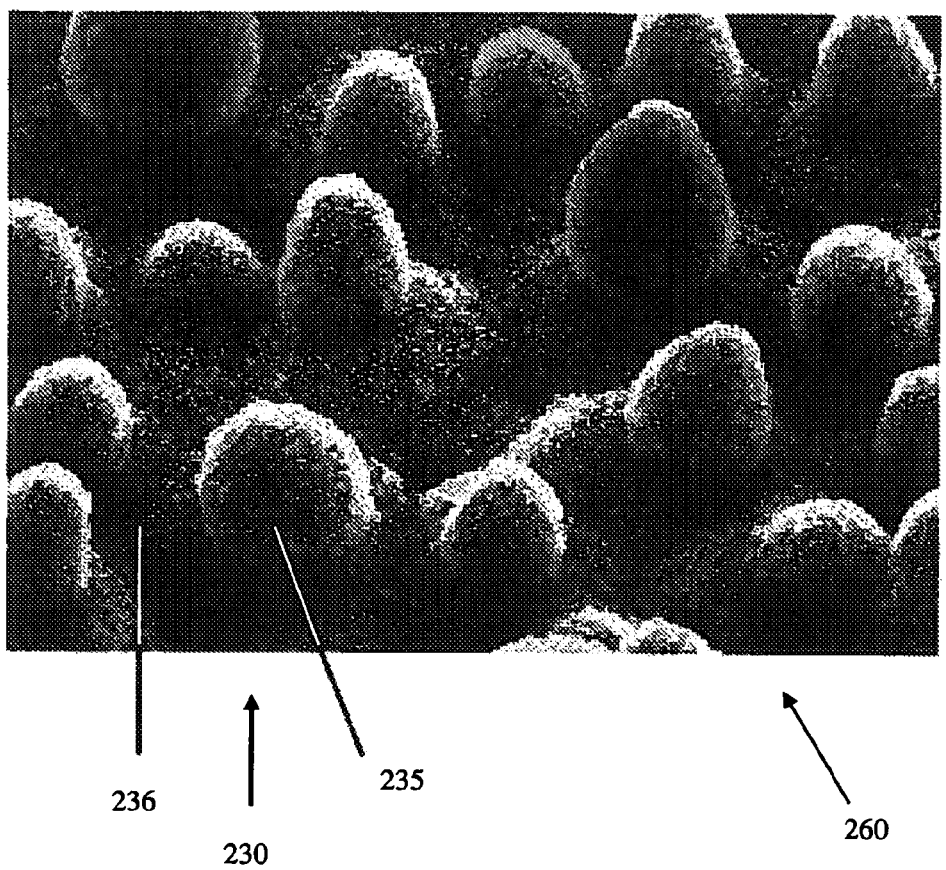
FIG. 4A is a representation of an SEM micrograph of nanostructures on the surface of a lotus leaf as viewed under a microscope.

FIG. 4A shows another example of a surface that includes nanostructures 230. The nanostructured surface illustrated in FIG. 4A is an SEM micrograph of nanostructures 230 arranged in a substantially continuous layer on a lotus leaf 260. The nanostructures 230 may comprise elevations 235 and depressions 236. The nanostructures 230 shown in FIG. 4A are generally conically shaped, but it is to be understood that the nanostructures 230 suitable for use with DTAs disclosed herein may comprise any suitable shape or combination of shapes.

Figure 4B:
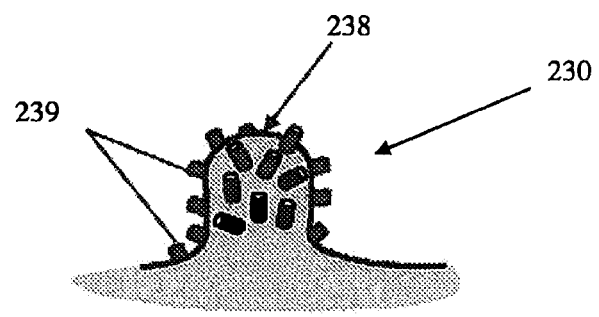
FIG. 4B is an illustration of the nanostructures of FIG. 4A.

FIG. 4B shows an illustration of the nanostructures 230 from FIG. 4A. The nanostructure 230 comprises a microscale bump 238 and nanoscale hair-like elements 239 on the bump. It is believed, without being limited by theory, that the bump 238 and hair-like elements 239 act cooperatively to provide the barrier properties associated with the surface of a lotus leaf (e.g., via creation of nanoscale elevations and depressions).

Figure 5:
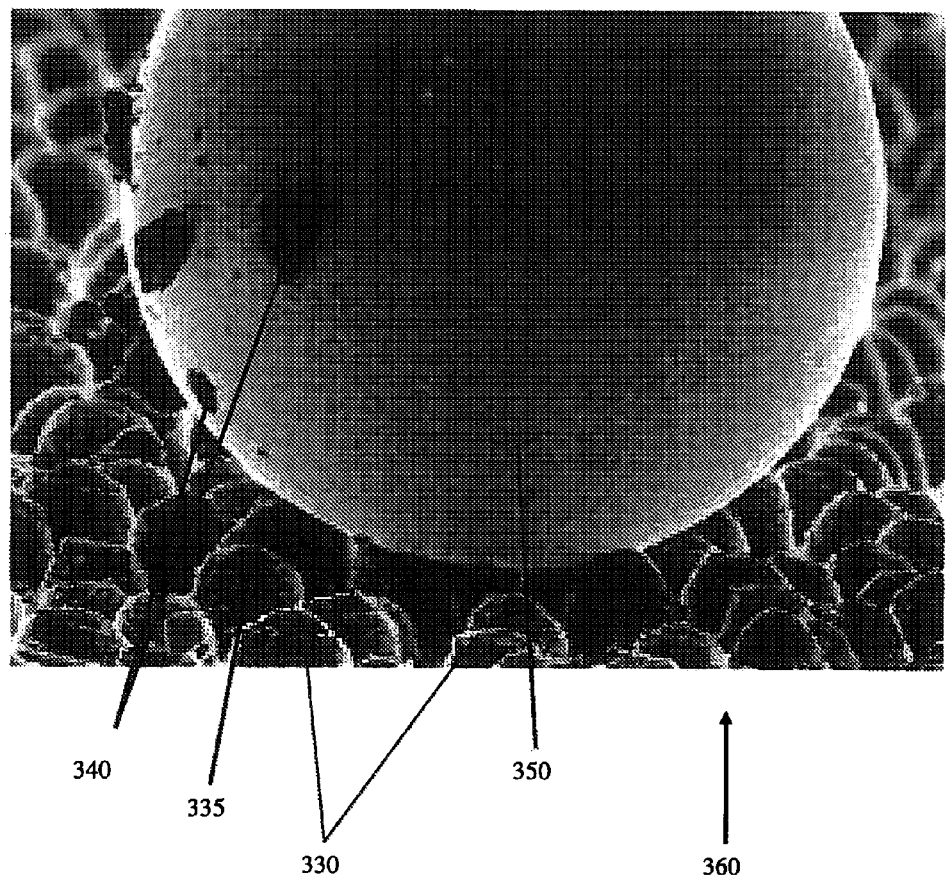
FIG. 5 is a representation of an SEM micrograph of a water droplet on a lotus leaf.

FIG. 5 shows an SEM micrograph of nanostructures 330 arranged in a substantially continuous layer on a lotus leaf surface 360. The nanostructures 330 comprise elevations 335 which are shown supporting a droplet of water 350. Without being limited by theory, it is believed that due to the surface tension of the water droplet 350 and the relatively low surface energy provided by the nanostructures 330, the water droplet 350 forms a spherical shape to minimize its surface area. External forces acting on the water droplet 350 such as, for example, gravity or moving air may cause the water droplet 350 to move across the nanostructure 330 layer, for example, by rolling across the upper-most portion of the elevations 335 (i.e., the portion of the elevation 335 that extends furthest away from the lotus leaf surface 360). If the water droplet 350 moves across the nanostructures 330, any contaminants 340 disposed on the lotus leaf surface 360 may adhere to the surface of the water droplet 350.

The presence of nanostructures on the treated surface of a substrate such as a skin mimic substrate can typically be detected by Atomic Force Microscopy ("AFM"). AFM images may provide relatively accurate indications of the surface height and spatial distribution of nanostructures on the surface of a treated substrate. Mathematical descriptions for describing a surface function in terms of its textural properties such as directionality, peaks, valleys, and roughness are commonly known in the art. One example of such a mathematical description is:

$$Z_s = f_s(X, Y).$$

Where:

$Z_s$ is the surface height value $f_s$ is the function describing the surface height at a point of measurement X,Y are the planar coordinates of the surface point of measurement When a surface is treated to create nanostructures, the surface roughness function of the surface may be altered due to the nanostructures that are superimposed on the surface of the substrate. One approach to assessing the effect of forming nanostructures on the surface of a substrate is to compare the surface roughness of an untreated substrate surface to the surface roughness of the treated substrate surface. In certain embodiments, it may be desirable to use a substrate having a substantially flat surface such as, for example, a polished silicon wafer commonly used in the microelectronics industry. In certain embodiments, it may be desirable to use a substrate that is adapted or selected to simulate a biological surface such as skin or hair.

It is commonly known that human skin typically exhibits directionality due to the predominant direction of the "furrows" in the skin. It is believed, without being limited by theory, that treating skin with nanostructures may cause a reduction in the directionality of the treated skin, and therefore may indicate the presence of a suitable nanostructured layer on the skin. Table 1 below summarizes the results of directionality comparisons of a skin mimic sample with no NFM and a skin mimic sample treated with one bead of NFM. The NFM bead was a randomly selected, individual particle of VM2260 Aerogel, available from Dow Corning Corp., Midland, Mich. The particle was crushed and distributed in a relatively even manner over the surface of a 3×3 cm sample of skin mimic substrate. Suitable examples of skin mimic substrates are described in U.S. Publication No. 2007/0128255 to Belcher, et al. The change in directionality of the treated skin may be evidenced by a change in the angular spectrum. The angular spectrum is automatically generated using the image metrology software (SPIP) of the atomic force microscope. The angular spectrum is based on image input and is analyzed according to the method described in more detail below. The change in the angular spectrum may be represented as a ratio between the spectrum amplitude at 90° and the spectrum amplitude at another angle such as, for example, 30° and/or 150°. The directionality index ($Q_d$) in Table 3 is calculated according to the formula:

$$Q_d = \text{Amplitude at } 90°/(0.5*(\text{Amplitude at } 150°+\text{Amplitude at } 30°)).$$

Reducing the directionality index ($Q_j$) of a substrate surface by at least 50%, 60%, or even 70% may indicate that the treated substrate has a suitable nanostructured layer capable of delivering an anti-contamination benefit. As can be seen in Table 1, the application of the NFM to the skin mimic substrate resulted in a directionality index reduction of 60%.

TABLE 1

| Sample | Amplitude (nm) at 90° | Amplitude (nm) at 30° | Amplitude (nm) at 150° | Directionality Index ($Q_d$) | $Q_d$ % reduction |
|---|---|---|---|---|---|
| Control | 480 | 120 | 120 | 4.00 | — |
| One Bead | 300 | 200 | 180 | 1.58 | 60 |

Figure 6:
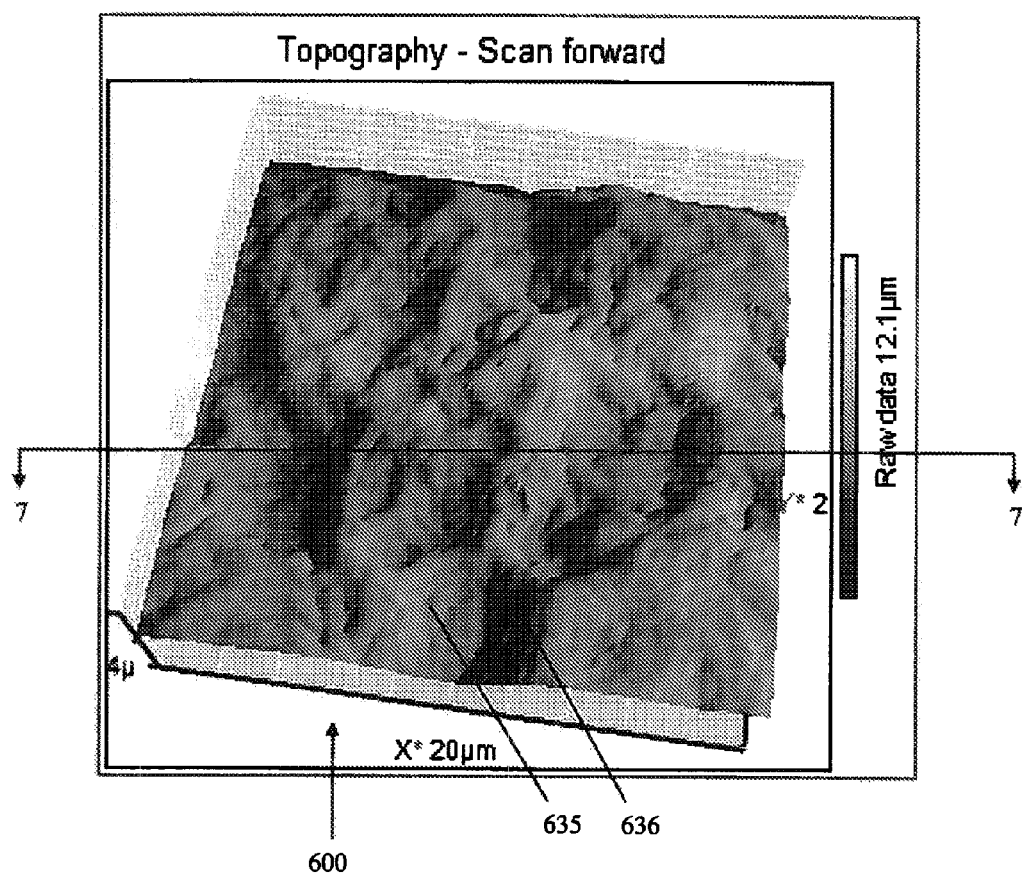
FIG. 6 is a representation of an AFM image of a substrate surface.
Figure 7:
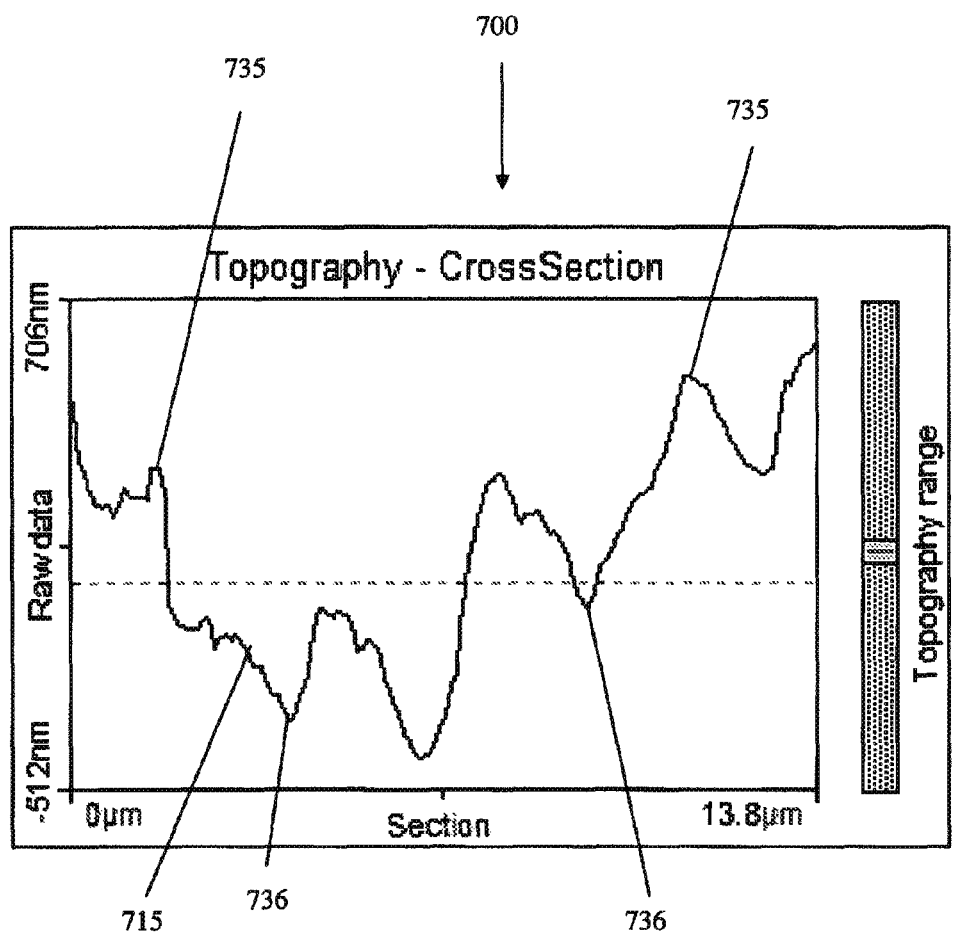
FIG. 7 is a graphical illustration of the topography of the substrate surface of FIG. 6.
Figure 8:
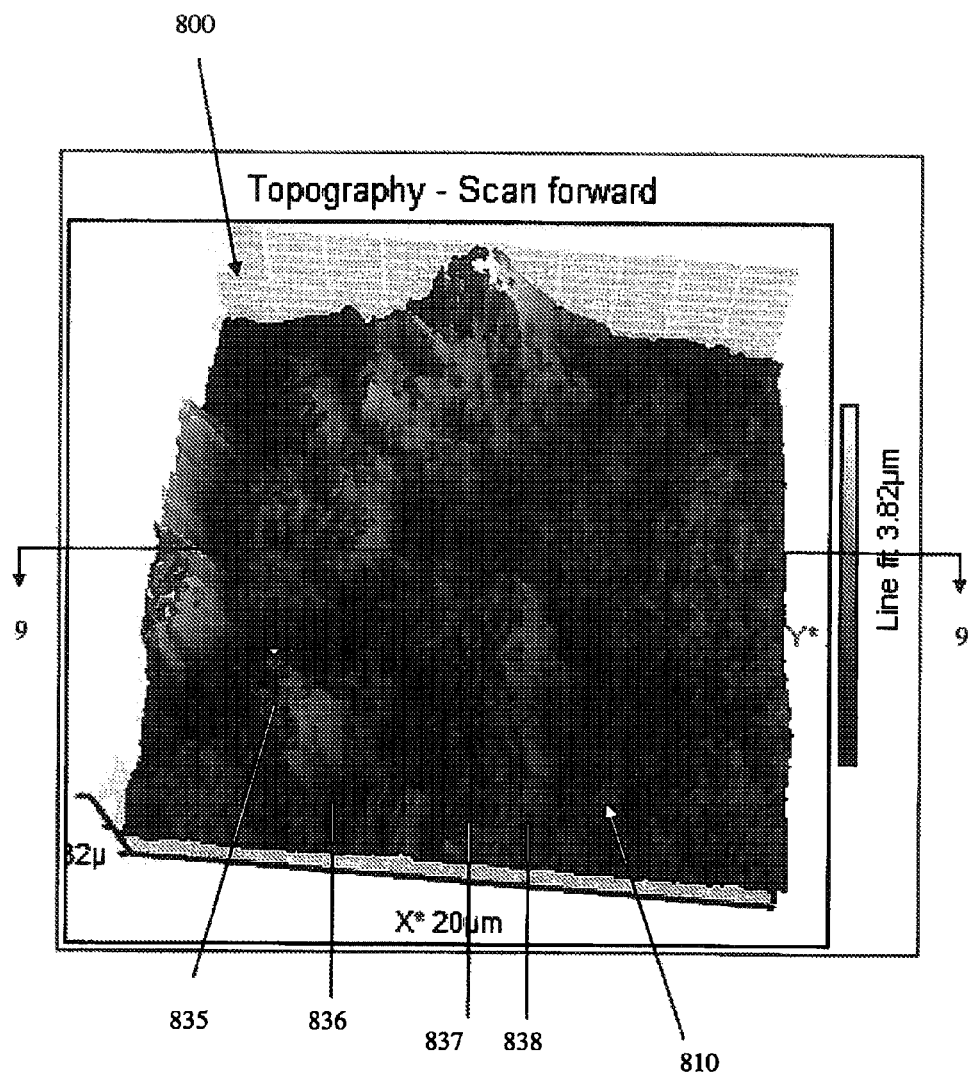
FIG. 8 is a representation of an AFM image of a substrate surface comprising a nanostructure forming material.

FIG. 6 shows an AFM image of a skin mimic surface 600 without an NFM disposed thereon. The AFM images depicted in FIGS. 6 and 8 are generated according to the procedure described in more detail below. The skin mimic surface 600 has a topography comprising various elevations 635 and depressions 636. FIG. 7 is graph 700 that shows a cross-sectional representation of the topography of the skin mimic surface 600 at line 7-7 in FIG. 6. The elevations 635 and depressions 636 of FIG. 6 are represented as high points 735 and low points 736 on the graph curve 715. The relative smoothness of the graph curve 715 is due to the substantial lack of nanostructures on the skin mimic surface 600. As can be seen from in FIG. 7, the heights of the elevations 635 and depth of the depressions 636 disposed on the skin mimic surface 600 of FIG. 6 may range between about 0.5 μm and 1 μm.

FIG. 8 shows an AFM image of a skin mimic surface 800 comprising an activated NFM 810 disposed thereon. The NFM 810 may comprise activatable, hydrophobic, silica aerogel particles. The substrate surface 800 may also include larger scale elevations 835 and depressions 836 that are the same or similar to a surface that does not include nanostructures such as, for example, substrate surface 600. The nanostructures disposed on the skin mimic surface 800 may provide smaller nanoscale elevations 837 and depressions 838. It is believed, without being limited by theory, that the smaller scale elevations 837 and depressions 838 give the skin mimic surface 800 a rougher appearance (as viewed on a cross-sectional graphical representation) than the skin mimic surface 600 of FIG. 6.

Figure 9:
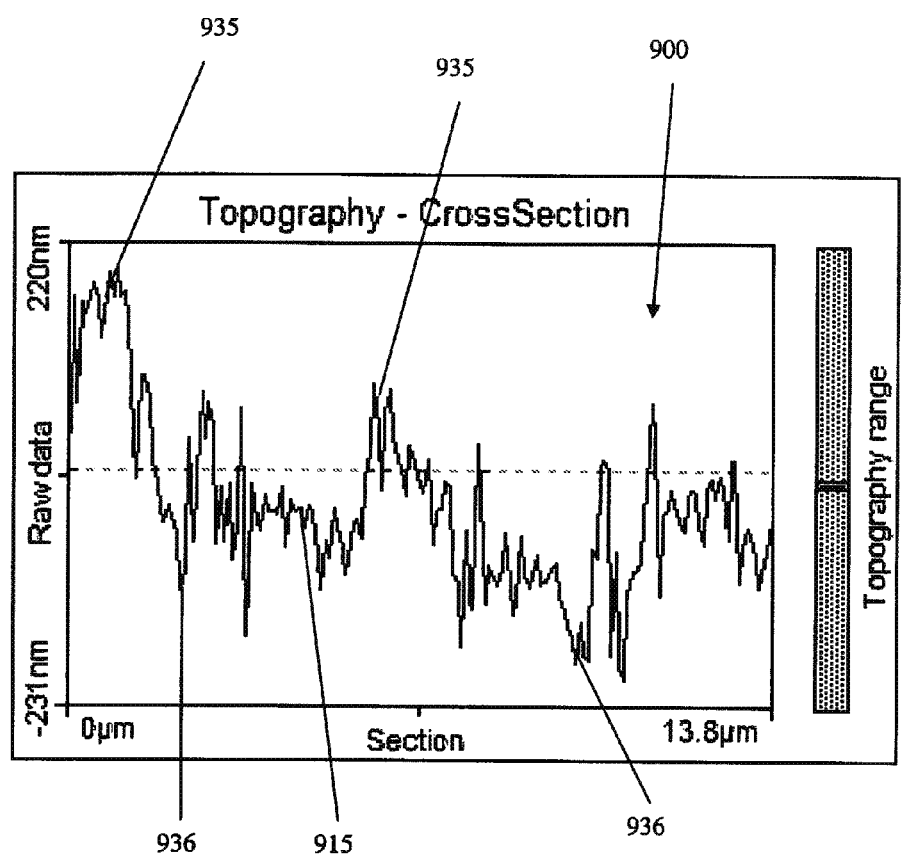
FIG. 9 is a graphical illustration of the topography of the substrate surface in FIG. 8.

FIG. 9 is graph 900 that shows a cross-sectional representation of the topography of the skin mimic surface 800 at line 9-9 in FIG. 8. The elevations 835 and depressions 836 of FIG. 8 are represented as high points 935 and low points 936 on the graph curve 915. Unlike the relatively smooth graph curve 715 shown in FIG. 7, the relatively rough graph curve 915 of FIG. 9 reflects the nanotopography imparted to the skin mimic surface 800 by the nanoscale elevations 837 and depressions 838. As seen in FIG. 9, the size (i.e., height and/or depth) of the nanoscale elevations 837 and depressions 838 may span a range of between about 50 nm to 200 nm.

Figure 10A:
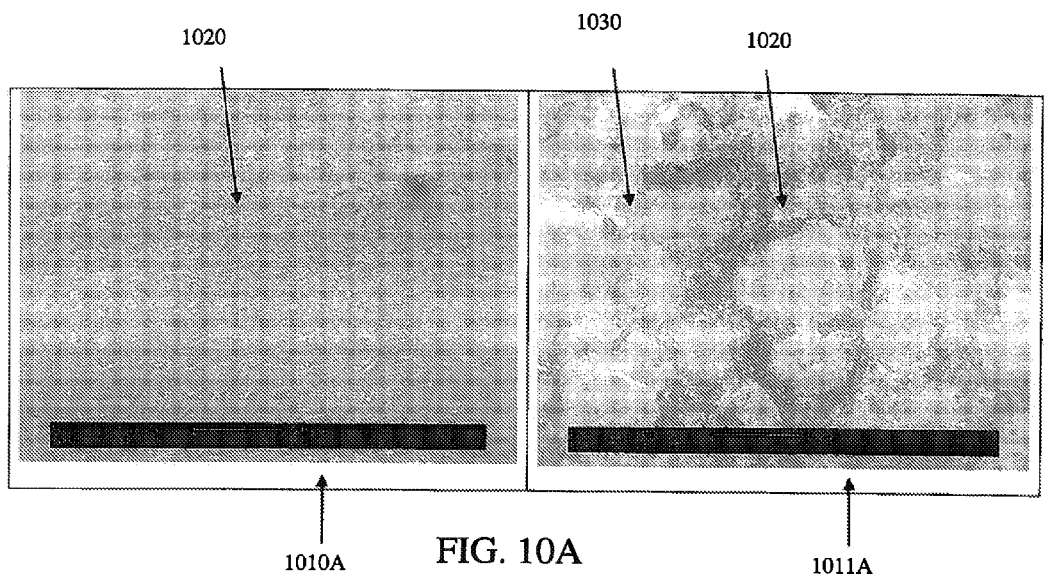
FIGS. 10A, 10B, and 10C are representations of SEM micrographs of a substrate surface and the substrate surface comprising a nanostructure forming material.
Figure 10B:
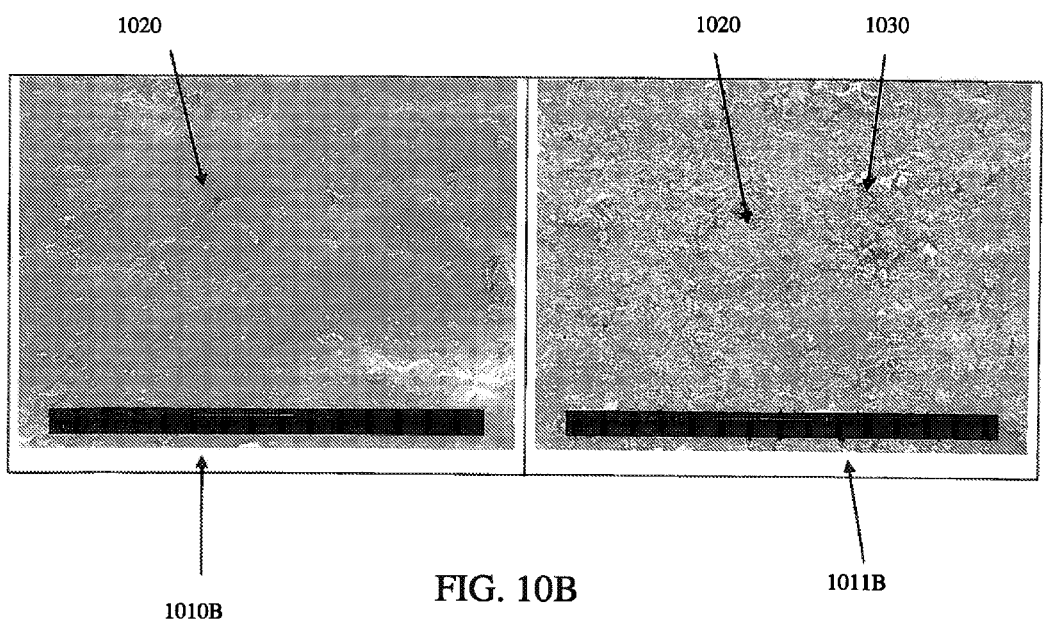
Figure 10C:
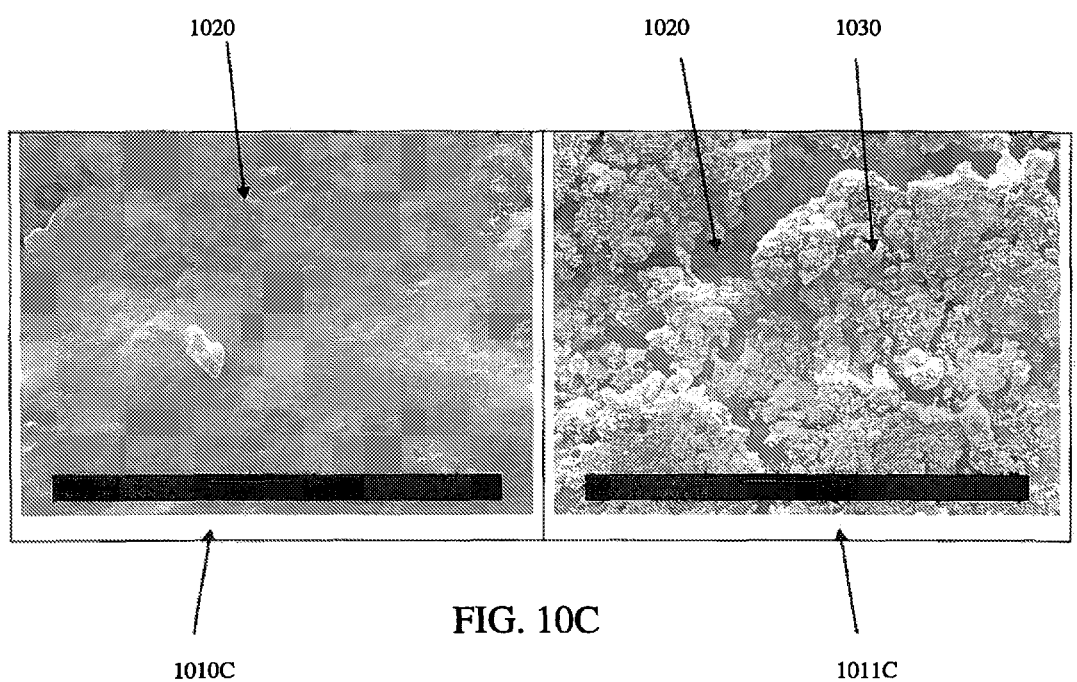

FIGS. 10A, 10B, and 10C show side-by-side SEM micrographs of a substrate surface 1020 (in this example a powder-free purple nitrile glove available from WVR International, West Chester, Pa.) without nanostructures 1030 and the same substrate surface 1020 with nanostructures 1030 (in this example an activated aerogel) at 44×, 2500×, and 10,000× magnification, respectively. In each of FIGS. 10A, 10B, and 10C, the left side SEM micrograph 1010A, 1010B, and 1010C, respectively, shows a substrate surface 1020 without nanostructures 1030. In each of FIGS. 10A, 10B, and 10C, the right side SEM micrograph 1011A, 1011B, and 1011C, respectively, shows the substrate surface 1020 with nanostructures 1030.

EXAMPLES

Unless otherwise indicated, the environmental conditions in the following Examples and test methods include a temperature of 23° C.±2° C. and a relative humidity of 50%±2%.

Example 1

Two grams of Cabot fine particle silica aerogel (grade 02N) (shown as NFM 1 in Table 1 below), available from Cabot Corporation, Boston Mass., are added to 18 grams of a 70% W/W ethanol in water solution and mixed for 1 minute in a Speed-Mixer DAC 400FV mixer, available from Flacktek Inc, Landrum, S.C., at the maximum speed setting to form a gel-like composition ("Gel A"). A mask made of silicone coated release paper having five parallel rectangular openings/holes measuring 6 mm in width and 300 mm in length, each opening separated from the others by 8 mm, is placed onto the wearing-facing surface of the topsheet of a Size 2, PAMPERS SWADDLERS NEW BABY brand disposable diaper, available from The Procter & Gamble Co., Cincinnati, Ohio. The openings in the mask are positioned 10 mm from the back waist edge of the diaper and extended toward the front of the diaper in a direction generally parallel to the longitudinal axis of the diaper. One-fifth of the total amount of Gel A, approximately 0.4 g, is applied manually with a finger covered by a powder-free finger cot in an even distribution to the entire exposed region of the topsheet through one of the openings in the mask. This process is repeated for the remaining four openings/topsheet sections. In total approximately 2.0 g of Gel A is applied to the diaper. The mask is then removed and the diaper is placed in a 40° C. oven for 1 hour so that the ethanol and water in Gel A could evaporate, thereby leaving the NFM adhered to the topsheet surface. The basis weight of the NFM is approximately 22 g/m² in the treated area of the diaper (i.e., 0.2 g of NFM powder over five mask openings of 6 mm×300 mm each). In this example, the area of the topsheet comprising the NFM is selected to be in the crotch region of the diaper in order to increase the likelihood of the NFM contacting the buttock and/or genital area of a wearer when the diaper is placed on the wearer. However, it is to be understood that the NFM may be disposed on any suitable diaper element or combination of elements in any suitable location and/or amount, as desired. Typically, the cumulative area of the diaper surface comprising the NFM is in the range of 15 cm² to 500 cm²

Example 2

A diaper and applied template as described in Example 1 is prepared for this example. Super White Protopet petrolatum, available from Witco Corporation, Greenwich, Conn., is applied via finger cot to the exposed topsheet in the mask openings in a thin layer (390 g/cm²). The petrolatum is used to represent a skin care composition or lotion carrier. VM2260 Aerogel beads (shown as NFM 2 in Table 1 below), available from Dow Corning Corp., Midland, Mich. are applied in an even layer at about 220 g/m² to the petrolatum containing areas of the topsheet. A finger cot covered finger is used to gently press the beads into the petrolatum such that at least some of the beads are immobilized in the petrolatum. While some of the beads may be completely immersed in the petrolatum, at least some of the immobilized beads are only partially immersed in the petrolatum. In other words, at least some of the immobilized beads have one or more portions of their surface area substantially free of petrolatum and exposed to the air. The mask is removed and compressed air at a pressure of less than 703 g/cm² is used to gently blow the remaining loose beads off the diaper, resulting in a substantially even layer of beads having a basis weight of approximately 22 g/m².

Example 3

0.5 grams of Cabot fine particle silica aerogel (grade 02N) (NFM 1) are added to 9.5 grams of a 70% W/W ethanol in water solution and mixed in a mixer (see Example 1) for 1 minute at the maximum speed setting to form Gel B. A BOUNTY brand paper towel, available from The Procter and Gamble Company, Cincinnati Ohio, is folded into fourths, forming a substrate 4 layers thick and 140 mm by 140 mm. A disposable plastic transfer pipet is used to pipet 40.0 g of Gel B onto the paper towel such that 5 beads of substantially equal weight are spaced 25 mm apart on the paper towel. The five beads are formed into a film by manually spreading the beads with a finger covered by a powder-free finger cot such that Gel B is evenly distributed over the entire top surface of the paper towel substrate. The sample is left on a lab bench at ambient conditions for 24 hours, allowing the water and ethanol to evaporate, thereby leaving 10 g/m² of NFM adhered to the surface of the paper towel.

Example 4

Pressure sensitive adhesive such as H2031, available from Bostick Findley, Wauwatosa Wis., is applied in a spiral pattern to a piece of silicone treated release paper. The adhesive is then transferred to a piece of 15 gsm spunbond polypropylene nonwoven with dimensions of 370 mm by 130 mm, available from Polymer Group Inc., Charlotte, N.C. 0.2 g of VM2260 large particle Aerogel (NFM 2), is sprinkled onto the adhesive coated non-woven, forming a mound of beads 2 cm by 6 cm. A second, substantially identical piece of nonwoven is placed on top of the first nonwoven, covering the beads. The edges of the second nonwoven piece are substantially aligned with the edges of the first nonwoven piece to form laminate A. The edges of Laminate A are sealed by using a roller to apply pressure to a one-inch wide strip around the perimeter of the laminate. Both barrier leg cuffs are removed from a size 2 PAMPERS SWADDLERS NEW BABY brand disposable diaper. Transfer tape (e.g., product #1524, available from 3M, St. Paul, Minn.) is applied around the perimeter of Laminate A to provide a 0.635 cm wide strip of adhesive. Laminate A is attached to the wearer-facing side of the diaper topsheet by placing laminate A on top of the adhesive. Laminate A is positioned such that it is substantially centered on the diaper in both the longitudinal direction (i.e., the longest dimension) and the direction orthogonal thereto (i.e., cross direction). A hand roller is used to apply a moderate pressure of approximately 1000 g/cm$^2$ around the perimeter of laminate A to ensure sufficient bonding.

Example 5

An OLAY daily facial wipe, available from Procter and Gamble, Cincinnati Ohio is folded into fourths, forming a substrate that is 4 layers thick and approximately 95 mm by 75 mm. 2.0 g of Gel B is added to the substrate in 5 beads of 0.4 g each. The beads are spread into a film manually with a finger covered by a powder-free finger cot such that Gel B is distributed evenly over substantially the entire top surface of the wipe. The sample is left on a lab bench at ambient conditions for 24 hours, allowing the water and ethanol to evaporate, thereby leaving approximately 14 g/m$^2$ of NFM adhered to the substrate surface.

Example 6

It is believed, without being limited by theory, that using a facial tissue or toilet tissue to apply an NFM to a bodily surface would also result in the formation of a suitable nanostructured layer on the bodily surface for providing an anti-contamination benefit. Suitable examples of facial and toilet tissue include PUFFS brand facial tissue and CHARMIN ULTRA brand toilet tissue, both available from The Procter and Gamble Company, Cincinnati, Ohio. The facial and toilet tissue substrates are prepared according to Examples 3, except that the facial tissue or toilet tissue substrate is used in place of the paper towel substrate of Example 3.

Example 7

In this example, a laminate structure may be used to entrap an NFM between layers of the laminate. A first substrate is prepared according to one of Examples 3 or 6. After the alcohol and water have evaporated (i.e., after the 24-hour drying period), a second, similar or substantially identical substrate (absent any NFM or gel) is joined to the first substrate in a face to face relationship such that the NFM is disposed between the first and second substrates. The second substrate is adhesively joined to the first substrate by applying TT5000B brand adhesive, available from HB Fuller to one surface of the second substrate via a spraying process. The adhesive is applied in a substantially uniform manner at a rate of 4.5 mg/meter per nozzle. The adhesive-treated surface of the second substrate is placed over the NFM-treated surface of the first substrate and then rolled with a 2 kg HR-100, ASTM 80 shore, rubber-faced roller for two full strokes (i.e., back and forth) at a speed of 10 mm/sec.

Table 1 summarizes the results of the BM Anti-Stick Test, described in more detail below, performed on an adult forearm. Table 1 illustrates, among other things, the anti-contamination benefit that may be achieved when an NFM is applied directly to skin and when an NFM is applied to skin by a DTA. The NFM in the NFM containing DTAs described in Examples 3 and 5 was applied according to the Modified Anti-Stick for Forearm Test Method described below. NFM 1 is a hydrophobic silica silyate Aerogel powder, grade 02N, available from Cabot Corporation, Boston, Mass. NFM 2 is a hydrophobic silica silyate aerogel bead, product # VM2260, available from the Dow Corning Co., Midland, Mich. NFM 3 is a fluorinated activated carbon, sample # YBR189-054 provided by the Cabot Corporation, Boston, Mass. NFM 4 is a hydrophobically modified, fumed silica, product number HDK H15 available from Wacker Chemi, Munich, Germany. Control 1 shows the anti-contamination level of skin with no applied NFM. Control 2 shows the anti-contamination level of skin after the application of a lotion comprising 41% stearyl alcohol, 57.9% petrolatum and 1.1% aloe extract.

TABLE 1

| | | NFM applied directly to Forearm | |
| --- | --- | --- | --- |
| Sample | Description | % Residual ABM on Skin (at add on of approx 300-1000 µg/cm$^2$) | % Residual ABM on Skin (at add on of approx 100-200 µg/cm$^2$) |
| NFM 1 | Cabot Fine Particle Silica Aerogel Grade 02N | NA | 1.5 |
| NFM 2 | VM2260 large Particle Silica Aerogel | NA | 3.2 |
| NFM 3 | Fluorinated Carbon | 0.78 | 9.6 |
| NFM 4 | Hydrophobic Fumed Silica | 5.67 | 34.42 |
| Example 3 | NFM 1 delivered by paper towel substrate | NA | 3.4 |
| Example 5 | NFM 1 delivered by facial wipe substrate | NA | 18.2 |
| Control 1 | No treatment | 33.8 | 33.8 |
| Control 2 | Lotion | 31.4 | 35.6 |

As can be seen in Table 1, NFMs (e.g., NFMs 1-4) on skin at various add-on levels may provide an anti-stick benefit versus non-NFM treated skin, including skin treated with a lotion or other skin care composition. At low add-on levels it can be seen that the silica aerogels, which are examples of crushable nanoporous NFMs, exhibited the best cleaning performance. Also shown in Table 1, NFMs delivered to skin via a substrate such as an absorbent treatment article or disposable cleaning article provided an anti-stick benefit. The forearm test used to generate the data in Table 1 is believed to simulate a typical usage condition for disposable cleaning and treatment articles. In addition, the BM analog is believed to be representative of many other biological and non-biological contaminants of bodily surfaces. However, it is to be understood that the present disclosure contemplates other usage conditions associated with disposable cleaning and treatment articles as well as other commonly known contaminants.

Table 2 summarizes the results of the BM ANTI-STICK TEST performed on an adult popliteal fossa (i.e., surface of the back of the knee). Table 2 illustrates, among other things, the anti-contamination benefit that may be provided by a DTA comprising an NFM. The first three samples in Table 2 were prepared according to the procedure described in Examples 1, 2, and 4. Control 1 is a Size 1 PAMPERS SWADDLERS NEW BABY brand disposable diaper with no NFM treatment. Control 2 is a size 1, HUGGIES SNUG 'N DRY brand disposable diaper available from the Kimberly-Clark Corporation, Neenah, Wis., with no NFM treatment.

TABLE 2

| Sample | NFM Treatment | % Residual ABM on Skin (at add on of approx 100-200 μg/cm$^2$) |
| --- | --- | --- |
| Example 1 | Delivered by diaper topsheet substrate | 2.8 |
| Example 2 | Delivered by diaper topsheet substrate | 25.1 |
| Example 4 | Delivered by nonwoven laminate | 5.5 |
| Control 1 | N/A | 35.5 |
| Control 2 | N/A | 38.6 |

As can be seen from Table 2, the articles comprising an NFM treatment delivered better anti-stick benefits to skin than the articles that did not include an NFM treatment. Samples 1, 2, and 3 show that an NFM may be delivered successfully (i.e., to form an effective nanostructured surface for contamination resistance) to the skin of a wearer by a diaper topsheet through multiple carrier/delivery approaches in quantities sufficient to provide a desired anti-stick benefit. The "behind the knee" Anti-stick Test Method used to generate the data in Table 2 is believed to represent the kinds of conditions (e.g., temperature, humidity, pressure, movement, friction, etc.) that the topsheet of an absorbent article is exposed to when worn by a wearer.

Test Methods
BM Anti-Stick Test Method

The objective of this test is to assess the adhesion of soils or exudates to skin by quantifying the percentage of residual artificial pasty bowel movement ("ABM"), formulated to be similar to real infant BM, left on the skin surface after treatment. When subjected to the BM Anti-stick Test, only part of the ABM typically remains on the skin surface and the rest of the ABM is typically removed. Ideally, the less ABM that remains, the more effective the treatment is.

One or more healthy adult panelists may participate in a single screening study. Each panelist completes a four-day washout period during which they use OLAY brand unscented moisturizing soap, available from The Procter and Gamble Company, Cincinnati, Ohio, to wash their forearms. Each panelist is directed to refrain from using any topical products such as ointments, creams, or lotions on their forearms during this washout-out period, including the day of testing. On the day of testing, each panelist's arms are inspected to ensure they are free of skin abnormalities such as cuts, scratches, and rashes. If any skin abnormalities are present, the panelist is not permitted to participate.

A template and a fine-tip marker are used to mark off between two and ten 3×3 cm sites on the hair-free volar forearms, i.e., with a maximum of 5 sites per forearm. All but one of these sites is treated with a composition comprising an NFM. Thus, 9 different NFMs may be tested per panelist. The remaining site receives no anti-stick treatment and serves as a negative control. Testing starts at the site closest to the elbow on the left arm and, as testing on each site is completed, progresses to the site closest to the wrist on the left arm, then to the site closest to the elbow on the right arm, and finally to the site closest to the wrist on the right arm. For each site treated, a predetermined amount of 300 μg/cm$^2$ of the NFM composition is applied in the center of the site with a powder-free finger cot, available from VWR Scientific of West Chester, Pa., Catalog #56613-413. The applied NFM composition is then spread over the entire site (the boundary of which is defined by the marks made using the template) by placing the finger cot on top of the agent or NFM composition and lightly rubbing the finger cot over the skin surface using several side-to-side and up-and-down movements for a total elapsed time of 10-15 seconds. Examining the site from an oblique angle, the tester ensures that a uniform film has been formed over the entire area of the site. The film is left exposed to air, untouched, for approximately 1 minute prior to application of the ABM.

A 1 ml syringe, with an opening approximately 1.5 mm in diameter, such as Catalogue #BD-309628 from VWR Scientific, West Chester Pa. filled with room temperature (about 21° C.) ABM and devoid of air bubbles, is placed on a tared analytical balance accurate to four decimal places. The weight of the ABM is recorded. The syringe with ABM is held over the center of the test site on the forearm between 5 and 10 mm from the surface of the skin and 0.2 ml of ABM is dispensed onto the skin by pressing the plunger and by watching the gradations on the syringe. When dispensed correctly, the ABM forms a reasonably uniform, compact mound in the center of the test site. The syringe is re-weighed on the analytical balance, and the weight is recorded. The quantity of ABM that was delivered to the forearm is calculated by subtracting the second weight from the first.

A 4×4 cm piece of weigh paper, Catalog #12578-201, available from VWR Scientific of West Chester, Pa., is tared on the analytical balance, centered over the ABM mound on the forearm test site, and gently lowered onto the ABM using forceps. The weigh paper must not be touched with fingertips, as this may transfer oils onto its surface. Next, a 500 g bottle-shaped weight, Catalog #12766-518, available from VWR Scientific of West Chester, Pa., configured to provide a pressure of approximately 35 g/cm$^2$, is placed over the weigh paper such that the mound of ABM under the weigh paper is approximately centered under the weight. The weight may be gently held in place or balanced on the forearm for 30 seconds. After 30 seconds have elapsed, two fingers are placed gently on either side of the weigh paper to hold it in place, and the 500 g weight is slowly lifted. Using a pair of forceps, the weigh paper is slowly and gently peeled from the test site. The forceps are placed at the lower right corner of the weigh paper, and the weigh paper is slowly (e.g., 1-2 seconds) peeled upwards in the direction of the upper left corner of the weigh paper at an angle of between 30° and 65°. Once removed, the weigh paper is placed back onto the analytical balance, and the weight is recorded to determine the amount of ABM removed. To prevent drying of the ABM, no more than 2 minutes may elapse between the application of ABM to the forearm test site and placement of the weigh paper and weight on the ABM.

The above steps are repeated until all of the test sites for each panelist have been tested. For the no-treatment control, application of the NFM composition is skipped and ABM is applied directly to the skin site. The weight percent (%) residual ABM left on the skin surface after treatment is calculated from the weight measurements according to the equation %Residual ABM=((ABM Applied−ABM Removed)/ABM Applied)×100.

The mean value for residual ABM and standard error of the mean for each NFM composition and for all panelists is calculated. When the method is run correctly, the no treatment control typically yields a value between approximately 30% to 35% residual ABM. Suitable environmental conditions for this test are a temperature of 21° C.±2° C. and a relative humidity of 30-50%.

Modified Anti-Stick for Forearm

In a variation of the BM Anti-Stick Test Method described above, an NFM may be applied to a substrate and transferred to the forearm of a panelist by rubbing the NFM containing substrate against the skin of the panelist's forearm. The protocol described above for testing on the forearm is followed except that, after marking of 3×3 cm sites on the forearm, the substrate containing the NFM is rubbed against the skin, directly over the test sites, using ten, back-and forth strokes with a gloved hand, applying moderate pressure of approximately 10 g/cm$^2$. The BM anti-stick test is then performed as described above and % of BM remaining on skin is calculated.

BM Anti-Stick Test Method (Behind the Knee)

The objective of this test is to assess the adhesion of soils or exudates to skin by quantifying the percentage of residual artificial pasty bowel movement ("ABM"), formulated to be similar to real infant BM, left on the skin surface after treatment of the skin with an NFM containing absorbent article. This test attempts to simulate the types of contact, pressure, and motion that may be experienced at the interface of a diaper topsheet and the skin of a wearer.

A diaper containing a NFM composition is applied to the popliteal fossa (back of the knee) of one or more panelists. The panelist is asked to stand so that the legs of the panelist are substantially straight. While the panelist is standing, position a diaper on the backside of a knee of the panelist such that the NFM containing portion of the topsheet of the diaper is substantially flat and in contact with the skin. Wrap the diaper around the leg and attach loosely at the knee-cap with 2.54 cm wide medical tape such as BLENDERM brand medical tape, available from 3M, St. Paul, Minn. A 10.16 cm by 162.56 cm elastic bandage is then wrapped around the leg such that then entire diaper and an area 2.54 cm above and 2.54 cm below the diaper are substantially covered. Secure the bandage with medical tape. Apply a second diaper to the other knee of the panelist in the same manner. This second diaper may contain an NFM or may be a diaper with no NFM for use as a negative control. After applying the diapers, the panelist may resume normal activities such as walking, standing, and sitting, which typically involve substantial bending and movement of the knee. However, activities that may cause substantial sweating must be avoided. Movement of the knee during normal activity is believed to create mechanical rubbing between knee and diaper topsheet, ideally, transferring the NFM to the skin. After two hours, the elastic bandage and diaper are removed are removed from the knees of the panelist, and the panelist is asked to lie down on a padded table. The BM anti-stick test is performed on the back of the knee using the same method as described above for testing on the forearm, except that no NFM is applied to the knee and only 2 sites are tested per panelists, one site on the back of each knee. The weight % of BM remaining on skin is calculated as described above.

Preparation of ABM

Obtain the Following:
  an analytical balance accurate to ±0.001 g
  a homogenizer capable of stirring the ingredients to homogeneity, such as a LABORTECHNIK T25 basic or equivalent as available from Ika-Werke GmbH and Co. KG of Staufen, Germany.
  a homogenizer probe to be used with the homogenizer, Catalog #S25N 25F, available from Ika-Werke GmbH and Co. KG of Staufen, Germany.
  6.6 g FECLONE brand synthetic fecal compound ("FC"), Powder #4, available from SiliClone Studio, Valley Forge, Pa., as Catalog Number Feclone BFPS-4.
  −6.6 g. FC, Powder #6, available from SiliClone Studio, Valley Forge, Pa., Catalog Number BFPS-6.
  6.6 g FC, Powder #7, available from SiliClone Studio, Valley Forge, Pa., Catalog Number BFPS-7.
  0.9 g CARBOPOL 981 brand rheology modifier, ("C-RM") available from BF Goodrich, Cleveland, Ohio.
  78.78 g. deionized water Procedure:

A. Preparation of C-RM Solution
1. Weigh 78.78 g±0.01 g of deionized water in a 250 ml beaker.
2. Weigh 0.900 g±0.001 g of C-RM on weigh paper.
3. Put beaker on a magnetic stirrer and set speed at 400 rpm.
4. Add C-RM powder slowly to the water, over the span of about 5 minutes. While adding the C-RM increase the stirring speed slowly to 600 rpm.
5. Once the C-RM powder has been added to the water, cover the beaker and continue mixing at 600 rpm for 15 minutes. The C-RM powder must be completely dispersed, i.e. a transparent gel without any agglomerates.
6. Set up a hot plate at 150° C. Place the C-RM solution on the hot plate and continue mixing at 600 rpm until the solution is heated to 81° C. to 83° C.

B. Preparation of ABM Mixture
1. Weigh 6.600 g±0.01 g each of FC powders #4, #6, and #7 into a beaker and mix well.
2. Using a T25 basic or equivalent homogenizer with a homogenizer probe, stir the C-RM solution at 8000 rpm for about 30 seconds before proceeding with Step 3.
3. To the C-RM solution that is being stirred, slowly add the FC powder mixture, about one quarter of the total at a time. Ensure that the FC powder mixture gets pulled through the homogenizer probe during addition, i.e. is thoroughly mixed into the pasty NFM composition that is forming. If necessary, use a spatula to facilitate incorporation of the FC powder mixture into the NFM composition.
4. After all of the FC powder mixture has been added, continue mixing with the homogenizer at 8000 rpm for an additional 5 minutes, using the spatula to push the pasty NFM composition towards the homogenizer probe. The NFM composition should be thoroughly mixed and appear homogeneous.

The finished ABM may be placed in a container, and stored in the refrigerator for up to 30 days. After 30 days, a new sample should be prepared for further experiments. The container must be tightly sealed to avoid drying out of the ABM. Prior to using the ABM in the Anti-Stick Screening Method, the ABM must be removed from the refrigerator and equilibrated to room temperature. An easy way to accomplish this is to fill a 10 ml syringe with cold ABM and then allow the syringe to equilibrate to room temperature on a counter top. Equilibration typically takes about 15 minutes. The 10 ml syringe can then be used to fill the 1 ml syringe described in the Anti-Stick Screening Method. If a syringe is not used immediately, the open end should be capped or otherwise sealed to prevent drying of the ABM. If condensation is present on the surface of the ABM, it should be stirred with a spatula to redistribute the condensed water prior to adding to the syringe.

Procedure Used to Generate AFM Images:
Sample Preparation:

A skin mimic substrate is cut into a 3×3 cm sheet. Two beads (~1 mm in diameter) of aerogel (which kind) were spread evenly on the surface of the skin mimic. The amount deposited ranged from 50 to 100 μg/$cm^2$. Skin mimic sample was transferred to AFM stage.

AFM Setup:

Nanosurf Nanite B atomic force microscope (Nanosurf AG, Switzerland) was used in batch mode. The batch mode scans selected areas on a surface. The scan size and scan setup is controlled by the operator in a batch file for high throughput data generation.

The tip for scanning was from AppNano, model ACLA (cantilever length 225 μm, width=40 μm, thickness=7 μm, frequency 145-230 kHz, n-type silicon with a reflective aluminum coating, spring constant is between 20-95 N/m, resistance: 0.001-0.025 ohm/cm). The tip is less than 10 nm in radius with a height of 12-16 μm.

The scan mode used is Dynamic Phase Contrast Mode (or tapping mode) at 10 seconds per line. Scan size is 20×20 μm. The scan direction was setup in the "UP" direction using 256 points and 256 lines (X-Slope 0, Y-Slope 0) with 5% over-scan. The constant height mode was disabled. During scanning, the operator used a set point 60% (with a P-Gain=15000 and I-Gain 1501). The vibrational amplitude was 0.2 V.

Images produced were analyzed using SPIP image metrology software for surface topography analysis.

Procedure Used to Generate SEM Images:

A scanning electron microscope was used to image the substrate with different magnification levels. All samples were sputter coated for 65 seconds. Images were obtained using an Environmental Scanning Electron Microscope (ESEM) at 2-3 kV.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable treatment article for contacting a bodily surface and improving the contamination resistance of the bodily surface, the disposable treatment article comprising:

one or more substrates comprising an activatable nanostructure forming material comprising one of a crushable nanoporous material or an aerogel, having a surface and wherein prior to activation, the nanostructure forming material has substantially no nanostructures on the nanostructure forming material's surface, the nanostructure forming material providing hydrophobic nanostructures to the bodily surface when the activatable nanostructure forming material is activated by activation means selected from the group consisting of: application of a crushing force, application of a shear force, application of a crushing pressure, and combinations thereof, and at least a portion of the nanostructure forming material is deposited on the bodily surface, the hydrophobic nanostructures comprising a plurality of nanoscale elevations and depressions, wherein the nanostructure forming material when activated and applied to the bodily surface reduces the adherence of a contaminant to the bodily surface;

wherein the nanostructure forming material comprises particles having an average particle size from 500 micrometers to 1 mm.

2. The disposable treatment article of claim 1, wherein the nanostructure forming material when activated and applied to the bodily surface reduces the adherence of a fecal analog to the bodily surface by at least about 50% when measured according to the BM Anti-Stick Test.

3. The disposable treatment article of claim 1, wherein the bodily surface on which the hydrophobic nanostructures are disposed has a water contact angle of greater than about 90° after the nanostructures are disposed on the bodily surface.

4. The disposable treatment article of claim 1, further comprising one or more carriers wherein the nanostructure forming material is at least one of suspended in and disposed on the one or more carriers.

5. The disposable treatment article of claim 4, wherein at least a portion of the carrier evaporates subsequent to being incorporated into the one or more substrates.

6. The disposable treatment article of claim 4, wherein at least one of the one or more carriers is selected from the group consisting of an emulsion, a liquid composition, the substrate, and combinations thereof.

7. The disposable treatment article of claim 6, wherein the liquid composition is selected from the group consisting of water, alcohol, and combinations thereof.

8. The disposable treatment article of claim 1, wherein at least one of the one or more carriers comprise at least one of a shampoo element, a soap element, a hair conditioner element, a skin conditioner element, a lotion element, a toothpaste element, a hair gel element, and a hair spray element.

9. The disposable treatment article of claim 1, wherein the activatable nanostructure forming material is activated by at least one of a shear force and a crushing force of greater than 0.1 N.

10. The disposable treatment article of claim 1, wherein the activatable nanostructure forming material is activated by a crushing pressure of greater than 6 $N/m^2$.

11. The disposable treatment article of claim 1, wherein the disposable treatment article is selected from the group consisting of toilet tissue, facial wipes, hand wipes, baby wipes, hair wipes, wet wipes, dry wipes, paper towels, facial tissue, sanitary napkins, panty liners, adult incontinence articles, training pants, diapers, finger cots, and disposable tooth brushes.

\* \* \* \* \*